(12) United States Patent
Lee et al.

(10) Patent No.: US 8,404,268 B2
(45) Date of Patent: Mar. 26, 2013

(54) LOCALLY TARGETED ANTI-FIBROTIC AGENTS AND METHODS OF USE

(75) Inventors: Elaine Lee, Santa Clara, CA (US); John Scott Surfus, San Mateo, CA (US)

(73) Assignee: Kyphon SARL, Neuchatel (CH)

( * ) Notice: Subject to any disclaimer, the term of this patent is extended or adjusted under 35 U.S.C. 154(b) by 133 days.

(21) Appl. No.: 12/911,967

(22) Filed: Oct. 26, 2010

(65) Prior Publication Data

US 2012/0101325 A1 Apr. 26, 2012

(51) Int. Cl.
*A61F 2/02* (2006.01)
(52) U.S. Cl. ......................................................... 424/426
(58) Field of Classification Search .......................... None
See application file for complete search history.

(56) References Cited

U.S. PATENT DOCUMENTS

| | | | |
|---|---|---|---|
| 3,883,140 A * | 5/1975 | Becker | 273/331 |
| 4,624,255 A | 11/1986 | Schenck et al. | |
| 4,863,457 A | 9/1989 | Lee | |
| 5,522,844 A | 6/1996 | Johnson | |
| 5,626,838 A | 5/1997 | Cavanaugh, Jr. | |
| 5,759,583 A | 6/1998 | Iwamoto et al. | |
| 5,868,789 A | 2/1999 | Huebner | |
| 5,942,241 A | 8/1999 | Chasin et al. | |
| 6,069,129 A | 5/2000 | Sandberg et al. | |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,756,058 B2 | 6/2004 | Brubaker et al. | |
| 6,773,714 B2 | 8/2004 | Dunn et al. | |
| 6,921,541 B2 | 7/2005 | Chasin et al. | |

(Continued)

FOREIGN PATENT DOCUMENTS

WO 2009111066 A1 9/2009

OTHER PUBLICATIONS

D. Ewen Cameron M. D., L. Levy M. D. and W. Hunzinger M.D.1 "Intrathecal Administration of Hyaluronidase: Effects Upon the Behavior of Patients Suffering From Senile and Arteriosclerotic Behavior Disorders", Am J Psychiatry 113:893-900, Apr. 1957 doi: 10.1176/appi.ajp.113.10.893, 1 The Allan Memorial Institute of Psychiatry, 1025 Pine Avenue West, Montreal, Canada. 1 pg.

(Continued)

*Primary Examiner* — Carlos Azpuru
(74) *Attorney, Agent, or Firm* — Sorell, Lenna and Schmidt LLP

(57) ABSTRACT

Effective devices and methods using an antifibrotic agent are provided for treating fibrosis or treating normal fibrous tissue. The devices and methods comprise an antifibrotic agent to degrade shrink, relax or stretch at least a portion of the fibrotic tissue. In some embodiments, the methods and devices are configured to immediately release an effective amount of the antifibrotic agent within 24 hours. In some embodiments, when the device comes in contact directly or indirectly with an activator, the antifibrotic agent will be immediately released from the depot. In some embodiments, the depot provides sustained release of the antifibrotic agent over a period of up to one year to treat fibrous tissue.

17 Claims, 3 Drawing Sheets

U.S. PATENT DOCUMENTS

| | | | |
|---|---|---|---|
| 6,958,149 B2 | 10/2005 | Vukicevic et al. |
| 6,974,462 B2 | 12/2005 | Sater |
| 7,132,098 B2 | 11/2006 | Masuda et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 7,572,440 B2 | 8/2009 | Vukicevic et al. |
| 2002/0009454 A1 | 1/2002 | Boone et al. |
| 2002/0090398 A1 | 7/2002 | Dunn et al. |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0072799 A1 | 4/2004 | Li et al. |
| 2004/0082540 A1 | 4/2004 | Hermida Ochoa |
| 2004/0109893 A1 | 6/2004 | Chen et al. |
| 2004/0214793 A1 | 10/2004 | Hermida Ochoa |
| 2004/0268425 A1 | 12/2004 | Bookbinder et al. |
| 2005/0142163 A1 | 6/2005 | Hunter et al. |
| 2005/0175709 A1 | 8/2005 | Baty, III et al. |
| 2005/0186261 A1 | 8/2005 | Avelar et al. |
| 2005/0197293 A1 | 9/2005 | Mellis et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0091207 A1 | 4/2008 | Truckai et al. |
| 2009/0214505 A1 | 8/2009 | Bookbinder et al. |
| 2010/0003237 A1 | 1/2010 | Keller et al. |
| 2010/0003238 A1 | 1/2010 | Frost et al. |

OTHER PUBLICATIONS

Fernández Cañabate E., Longoni Merino M., Garriga Biosca R., Navas Vinagre I. "Administration of intrathecal hyaluronidase in a patient diagnosed with adhesive arachnoiditis" Farm Hosp. Jan.-Feb. 2008;32(1):58-60. Spanish. No abstract available. PMID: 18426706 [PubMed—indexed for MEDLINE] Free Article Related citations. 3 pgs.

Gourie-Devi M, Satishchandra P., "Hyaluronidase as an adjuvant in the management of tuberculous spinal arachnoiditis". J Neurol Sci. Mar. 1991;102(1):105-11.PMID: 1856727 [PubMed—indexed for Medline] Related citations, 1 pg.

Gourie-Devi M, Satish P., "Intrathecal hyaluronidase treatment of chronic spinal arachnoiditis of noninfective etiology". Surg Neurol. Sep. 1984;22(3):231-4.PMID: 6547785 [PubMed—indexed for MEDLINE] Related citations, 1 pg.

Gegalian L., "Use of hyaluronidase in the central nervous system." Surg Neurol. Jul. 1979;12(1):3-5.PMID: 451858 [PubMed—indexed for Medline] Related citations, 1 pg.

Gleeson, Pauls, "Obstetrical Physical Therapy", Physical Therapy, vol. 68 / No. 11, Nov. 1988, 4 pgs.

Siegal, Rengachary, "Carpal Tunnel Symdrome in Pregnancy", Thieme 1996, Neurosurgical aspects of pregnancy, Issue 494, 5 pgs.

Whitesell, London, "Neuromuscular complications of pregnancy", Medlink 2008, 7 pgs.

AMA CSA, "Effects of work on pregnancy", 1999, 19 pgs.

Rose, "Carpal Tunnel Syndrome relieved by pregnancy", British Medical Journal, Mar. 31, 1956, 744-745, 2 pgs.

Bjorkqvist, Lang, Punnonen, Rauramo, "Carpal Tunnel syndrome in ovariectomized women.", AOGS 1977, 56(2)127-30., abstract, 1 pg.

Dekel, Papaionnou, Rushworth, Coates, "Idiopathic carpal tunnel syndrome caused by carpal stenosis", British Medical Journal, May 31, 1980, 3 pgs.

Samuel, "Relaxin: Antifibrotic Properties and Effects in Models of Disease", Clinical Medicine & Res., vol. 3, No. 4: 241-249, 2005, 9 pgs.

Halozyme Therapeutics, "Product Pipeline", 2010, 2 pgs.

* cited by examiner

LOCALLY TARGETED ANTI-FIBROTIC AGENTS AND METHODS OF USE

BACKGROUND

Fibroblasts are the major cell type responsible for the synthesis of collagen, a fibrous protein essential for maintaining the integrity of the extracellular matrix found in the dermis of the skin and other connective tissues. The production of collagen is a finely regulated process, and its disturbance may lead to the development of tissue fibrosis. The formation of fibrous tissue is part of the normal healing process after injury, including injury due to surgery. However, in some circumstances there is an abnormal accumulation of fibrous material such that it interferes with the normal function of the affected tissue.

Scar tissue serves only a structural role, but does not contribute to the function of the organ in which it appears. For example, in carpal tunnel syndrome, fibrosis scar tissue and/or swelling in or around the tendon sheaths that pass through the carpal tunnel can pressure on the medial nerve causing pain and numbness in the fingers.

Fibrotic growth can proliferate and invade healthy surrounding tissue, even after the original injury heals. In most cases fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

Stimulation of fibroblast activity is involved in the development of fibrotic conditions, including spontaneous and induced conditions. Abnormal accumulation of collagen in the extracellular matrix, resulting from excessive fibroblast proliferation and/or collagen production, can cause fibrosis of a number of tissues including the skin. Many common debilitating diseases, such as liver cirrhosis and pulmonary fibrosis, involve the proliferation of fibrous tissue as do certain skin diseases such as scleroderma, and the formation of adhesions, keloids, and hypertrophic scars.

Conventional treatment of most fibrosis frequently involves the administration of corticosteroids, such as prednisone, and/or other medications that suppress the body's immune system. The goal of current treatment regimens is to decrease inflammation and subsequent scarring. Responses to currently available treatments are variable, and the toxicity and side effects associated with these treatments can be serious. Indeed, few patients respond to corticosteroids alone, and immune suppression medications are often used in combination with corticosteroids.

Thus, there is a need to develop new devices and methods to treat fibrosis that allow accurate and precise implantation of the device at, near, or in the fibrous tissue resulting in minimal physical and psychological trauma to the patient.

SUMMARY

New devices and methods are provided for treating fibrosis that allow accurate and precise implantation of the device at, near, or in the fibrous tissue (including normal or abnormal fibrous tissue) resulting in minimal physical and psychological trauma to the patient.

In some embodiments, the antifibrotic agent can be administered in the same cannula or needle without the need to reposition it several times. The antifibrotic agent can directly or indirectly induce the degradation, shrinkage, relaxation, or stretching of the fibrous tissue.

In some embodiments, the devices and methods provided allow the device (e.g., drug depot) to be retrieved if implanted at the wrong site because the device will not be caused to release the antifibrotic agent until the device is implanted in the desired location.

In some embodiments, a device is provided for treating fibrosis in a patient in need of such treatment, the device being biodegradable and implantable at, near or in the fibrotic tissue, the device comprising an antifibrotic agent to degrade, shrink, relax, or stretch at least a portion of the fibrotic tissue and being configured to immediately release an effective amount of the antifibrotic agent within 24 hours.

In some embodiments, the device comprises a drug depot having an immediate release component that when it contacts an activator (e.g., liquid or semi-solid activator, energy, etc.), the activator causes the drug depot to release an effective amount of the antifibrotic agent.

In one embodiment, there is a device for treating fibrous tissue in a patient in need of such treatment, the device being biodegradable and implantable at, near, or in a fibrous tissue, the device comprising an antifibrotic agent to degrade, shrink, relax or stretch at least a portion of the fibrous tissue and being configured to immediately release an effective amount of the antifibrotic agent within 24 hours and configured to provide sustained release of the antifibrotic agent over a period of up to one year to treat the fibrous tissue. The device can treat normal and/or abnormal fibrous tissue.

In a second embodiment, there is a device for treating fibrous tissue in a patient in need of such treatment, the device being biodegradable and implantable at, near, or in a fibrous tissue, the device comprising an antifibrotic agent to degrade, shrink, relax and/or stretch at least a portion of the fibrous tissue and being configured to immediately release an effective amount of the antifibrotic agent within 24 hours; and an activator configured to contact the device and cause immediate release of the antifibrotic agent.

In a third embodiment, there is a method for treating fibrosis in a patient in need of such treatment, the method comprising administering an implantable and biodegradable device at, near, or in a fibrotic tissue, the device comprising an antifibrotic agent to degrade, shrink, relax, or stretch at least a portion of the fibrotic tissue and being configured to immediately release an effective amount of the antifibrotic agent within 24 hours on contact with an activator and administering the activator at, near, or in the fibrotic tissue so as to cause immediate release of the antifibrotic agent from the device.

In a fourth embodiment, there is a method for treating fibrosis, the method comprising administering an implantable and biodegradable device to the fibrotic tissue, the device comprising an antifibrotic agent to degrade, shrink, relax, or stretch at least a portion of the fibrotic tissue and being configured to immediately release an effective amount of the antifibrotic agent within 24 hours and to provide sustained release of the antifibrotic agent over a period of up to one year to treat the fibrotic tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
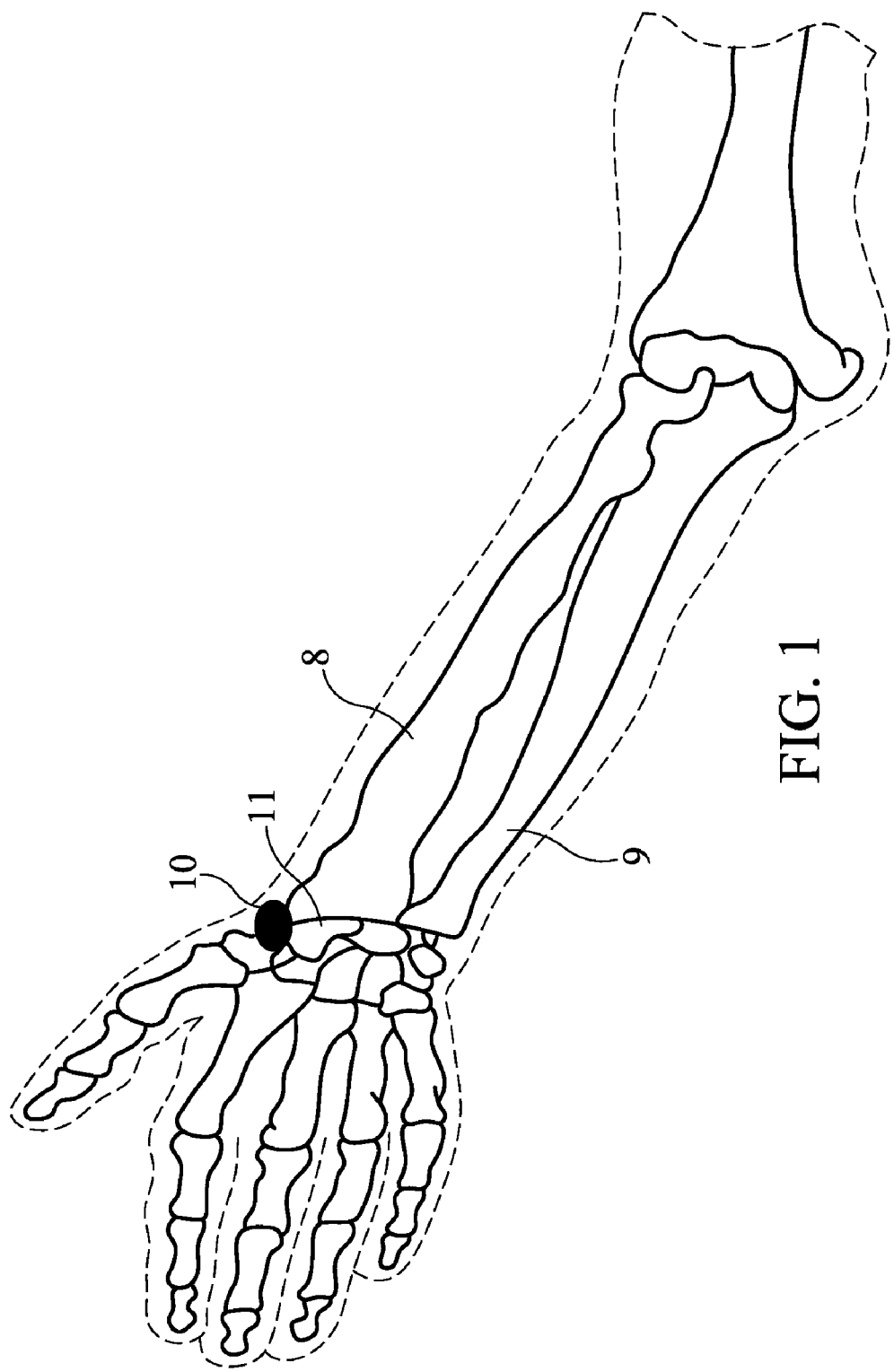
FIG. 1 illustrates an embodiment of a human radius and ulna showing a drug depot containing the antifibrotic agent implanted by the wrist bone near fibrous tissue, which can be healthy and unhealthy.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

An "implantable device" and expressions of like as utilized herein refers to any object implantable through surgical, medical, dental, injection, or other suitable means whose primary function is achieved either through its physical presence or mechanical properties. Implantable devices include one or more drug depots.

The term "antifibrotic agent" refers to one or more chemical or biological compounds that have antifibrotic activity in mammals. These compounds may have different mechanisms of action, some reducing the formation of collagen or another protein, and others enhancing the metabolism or removal of collagen in the affected area of the body. All such compounds having activity in the reduction of the presence of fibrous tissue are included herein, without regard to the particular mechanism of action by which each such drug functions.

An antifibrotic agent, includes, but is not limited to, an agent that degrades or causes the dissolution or shrinkage of fibrotic tissue or a portion thereof, such as for example, the fibrotic tissue in or surrounding the tendon sheaths that pass through the carpal tunnel. In some embodiments, the antifibrotic agent will stretch or relax fibrous tissue (e.g., normal or abnormal fibrous tissue). Abnormal fibrous tissue includes tissue that has an excessive amount or abnormal amount of fibrosis tissue. Normal fibrous tissue includes tissue that has a normal amount of fibrous tissue that is not pathological or indicative of disease. For example, in carpal tunnel syndrome, in some embodiments, the flexor retinaculum generally has normal amounts of fibrous tissue. However, it is beneficial to degrade this normal fibrous tissue so the flexor retinaculum can stretch more easily to accommodate the excess tissue within the carpal tunnel. In some embodiments, the antifibrotic agent can degrade, stretch, and/or relax the normal fibrous tissue, which can be beneficial in treatment of conditions such as scoliosis, tarsal tunnel syndrome, carpal tunnel syndrome and other conditions, where degrading, stretching and/or relaxing healthy or normal fibrosis tissue would be beneficial.

In some embodiments, the antifibrotic agent will enzymatically degrade or shrink the fibrotic tissue. For example, in some embodiments when the antifibrotic agent is an enzyme, it will reduce pressure by degrading proteoglycans (PG) so that PGs are not available to hold water. In some embodiments, the antifibrotic agent can be a protease or glycanase, which is not proteolytic. In some embodiments, the antifibrotic agent, instead of an enzyme, can be an agent that dehydrates the fibrotic tissue, such as for example, a polycationic polymer. In some embodiments, the anti-fibrotic agent may be a hormone, such as for example, relaxin, which inhibits collagen production and stimulates collagen degradation. In some embodiments, the anti-fibrotic agent may be a cytokine, drug, cell, or nucleic-acid-based material that influences the function, viability, or proliferation of fibroblasts or other cells in the fibrotic tissue. In some embodiments, the antifibrotic agent may be cells that inhibit collagen production and/or stimulates collagen degradation.

An "activator" refers to a substance or energy that increases the release of the antifibrotic agent from the device or increases the activity of the antifibrotic agent after it is released from the device. In some embodiments, the activator can be energy (kinetic, potential, thermal, gravitational, sound, elastic and/or electromagnetic energy) that is applied to the device or externally to the device (e.g., skin or tissue that surrounds the device) and causes immediate release or sustained release of the therapeutic agent. For example, the activator can be a wireless or wired electrical signal, electromagnetic radiation, magnetic field, acoustic energy, or ultrasonic energy when it comes in contact either directly or indirectly with the drug depot will cause release of the therapeutic agent.

"Analgesic" refers to an agent or compound that can reduce, relieve or eliminate pain. Examples of analgesic agents include but are not limited to acetaminophen, a local anesthetic, such as for example, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof. Analgesic agents also include those with analgesic and anti-inflammatory properties, such as, for example, amitriptyline, carbamazepine, gabapentin, pregabalin, clonidine, or a combination thereof. The device can include one or more analgesics.

The phrase "anti-inflammatory agent" refers to an agent or compound that has anti-inflammatory effects. The device can include one or more anti-inflammatory agents. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

The device can include one or more steroids. Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The device can include one or more statins. Examples of useful statins for treatment of pain and/or inflammation include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appin. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

In some embodiments, the anti-inflammatory agent can include an "anti-cytokine agent." An anti-cytokine agent includes any molecule, cell, or physical stimulus which decreases, blocks, inhibits, abrogates or interferes with the pro-inflammatory cascade of cytokine proteins leading to an inflammatory response. For example, a suitable "tumor necrosis factor alpha antagonist" or "TNF-alpha" antagonist can bind TNF, and includes anti-TNF antibodies and/or receptor molecules which bind specifically to TNF. A suitable TNF antagonist can also prevent or inhibit TNF synthesis and/or TNF release and includes compounds such as thalidomide, tenidap, or phosphodiesterase inhibitors, such as, but not limited to, pentoxifylline or rolipram.

Anti-cytokine agents include substances that are direct and local-acting modulators of the pro-inflammatory effect of TNF-alpha, such as but not limited to, soluble tumor necrosis factor alpha receptors, any pegylated soluble tumor necrosis factor alpha receptor, monoclonal or polyclonal antibodies or antibody fragments or combinations thereof. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1, 3-beta-D-glucans, Lenercept, PEG-sTNFRII Fc Mutein, D2E7, Afelimomab, or combinations thereof. They can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes. These substances can also act, for example, by blocking or antagonizing the binding of excitatory molecules to nociceptive receptors in the nervous system or neuromuscular system, as these receptors often trigger an inflammatory response to inflammation or injury of the nerve or surrounding tissue through a nitric oxide-mediated mechanism. These biological response modifiers include, for example, inhibitors of the action of tumor necrosis factor alpha (TNF-alpha).

In one example of an alternative approach, the anti-cytokine agent is a TNF binding protein. One suitable such anti-cytokine agent is currently referred to as Onercept, Onercept-like agents, and derivatives are all considered acceptable. Still other suitable anti-cytokine agents include dominant-negative TNF variants. A suitable dominant-negative TNF variant includes but is not limited to DN-TNF and including those described by Steed et al. (2003), "Inactivation of TNF signaling by rationally designed dominant-negative TNF variants," Science, 301(5641):1895-1898. Still more embodiments include the use of a recombinant adeno-associated viral (rAAV) vector technology platform to deliver the oligonucleotides encoding inhibitors, enhancers, potentiators, neutralizers, or other modifiers. For example, in one embodiment a rAAV vector technology platform delivers the DNA sequence of a potent inhibitor of tumor necrosis factor (TNF-alpha). One suitable inhibitor is TNFR:Fc. Other anti-cytokine agents interfere with one of the steps in the gene expression and secretion of cytokines, such as transcription, translation, folding, post-translational modification, and intracellular transport. For example, small anti-sense RNA or short interfering RNA (siRNA) can block post-transcriptional processing of cytokine genes.

Other anti-cytokine agents include antibodies, including but not limited to naturally occurring or synthetic, double chain, single chained, or fragments thereof. For example, suitable anti-cytokine agents include molecules are based on single chain antibodies called Nanobodies® (Ablynx, Ghent Belgium) which are defined as the smallest functional fragment of a naturally-occurring single domain antibody.

It is understood that TNF is both affected by upstream events which modulate its production and, in turn, affects downstream events. Alternative approaches to treating the fibrosis include using antagonists designed to specifically target TNF as well as molecules upstream, downstream and/or a combination thereof. Such approaches include, but are not limited to modulating TNF directly, modulating kinases, inhibiting cell-signaling, manipulating second messenger systems, modulating kinase activation signals, modulating a cluster designator on an inflammatory cell, modulating other receptors on inflammatory cells, blocking transcription or translation of TNF or other targets in pathway, modulating TNF-alpha post-translational effects, employing gene silencing, or modulating interleukins, for example IL-1, IL-6 and IL-8.

Interleukin-1 is a pro-inflammatory cytokine similar in action to TNF-alpha. For example, certain inhibitors of this protein are similar to those developed to inhibit TNF-alpha. One such example is Kineret® (anakinra) which is a recombinant, non-glycosylated form of the human interleukin-1 receptor antagonist (IL-1Ra). Another suitable anti-cytokine agent is AMG 108, which is a monoclonal antibody that blocks the action of IL-1.

Other suitable anti-cytokine agents include: integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, and HuMax IL-15 (anti-IL 15 antibody).

Unless otherwise specified or apparent from context, where this specification and the set of claims that follows refer to a drug (e.g., an antifibrotic agent, an anti-inflammatory agent, analgesic, or the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of a medical device (e.g., drug depot) containing an antifibrotic agent degrades the fibrotic tissue, which reduces pressure and, in some embodiments, allows retraction of the fibrotic tissue, which reduces pain and/or inflammation.

"Localized" delivery includes delivery where one or more devices (e.g., drug depots) containing at least the antifibrotic agent is deposited within a tissue, for example, a bone, muscles, ligament, tendon, blood vessel tissue, or in close proximity (within about 5 cm, or preferably within about 2 cm, for example) thereto. A "targeted delivery system" provides delivery of one or more drugs depots having a quantity of therapeutic agent that can be deposited at or near the target site (e.g., fibrotic tissue) as needed for treatment of pain, inflammation or other disease or condition.

The term "fibrosis" refers to the formation of fibrous tissue or "fibrotic tissue", usually as a reparative or a reactive process. As used herein, "fibrosis" or "fibroproliferative disease" includes those disorders or disease states that are caused by or accompanied by the abnormal deposition of scar tissue, or by excessive accumulation of collagenous connective tissue. In other embodiments, "fibrosis" includes formation of fibrous tissue that may be a normal part of an organ or tissue. Thus, the antifibrotic agent may be administered to normal or healthy fibrous tissue to provide benefit to the patient (e.g., stretching, relaxing tissue to reduce or prevent pain and/or inflammation). Fibrosis may occur in any organ including, for example, kidney, lung, liver, skin, central nervous system, bone, bone marrow, cardiovascular system, an endocrine organ or the gastrointestinal system. By "fibrosis-associated condition" is meant any condition that is related to fibrosis. Thus, fibrosis-associated conditions may be caused by, be concomitant with, or cause fibrosis.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Antifibrotic Agent

New devices and methods are provided for treating fibrosis that allow accurate and precise implantation of the device at, near, or in the fibrotic tissue (e.g., normal and/or abnormal fibrous tissue) resulting in minimal physical and psychological trauma to the patient.

In some embodiments, the antifibrotic agent can be administered in the same cannula or needle without the need to reposition it several times. The antifibrotic agent can directly or indirectly induce the degradation, shrinkage, relaxation, or stretching of the fibrotic tissue.

In some embodiments, the devices and methods provided allow the device (e.g., drug depot) to be retrieved if implanted at the wrong site because the device will not be caused to release the antifibrotic agent until the device is implanted in the desired location.

In some embodiments, the device comprises a drug depot having an immediate release component that when it contacts an activator (e.g. liquid or semi-solid activator), the activator causes the drug depot to release an effective amount of the antifibrotic agent.

In some embodiments, the antifibrotic agent can be administered in the same cannula or needle without the need to reposition it several times. The antifibrotic agent degrades the fibrotic tissue, which reduces pressure and, in some embodiments, allows retraction of the fibrotic tissue. Typically, these areas do not include the spine.

In one embodiment, there is a device for treating fibrosis in a patient in need of such treatment, the device being biodegradable and implantable at, near, or in a fibrotic tissue, the device comprising an antifibrotic agent to degrade, shrink, relax, or stretch at least a portion of the fibrotic tissue and being configured to immediately release an effective amount of the antifibrotic agent within 24 hours and configured to provide sustained release of the antifibrotic agent over a period of up to one year to treat the fibrosis.

In some embodiments, the antifibrotic agent will stretch or relax fibrous tissue (e.g., normal or abnormal fibrous tissue). For example, in carpal tunnel syndrome, in some embodiments, the flexor retinaculum generally has normal amounts of fibrous tissue. However, it is beneficial to degrade this normal fibrous tissue so the flexor retinaculum can stretch more easily to accommodate the excess tissue within the carpal tunnel. In some embodiments, the antifibrotic agent can degrade, stretch, and/or relax the normal fibrous tissue, which can be beneficial in treatment of conditions such as scoliosis, tarsal tunnel syndrome, carpal tunnel syndrome and other conditions, where degrading, stretching and/or relaxing healthy or normal fibrous tissue would be beneficial.

In a second embodiment, there is a device for treating fibrosis in a patient in need of such treatment, the device being biodegradable and implantable at, near, or in a fibrotic tissue, the device comprising an antifibrotic agent to degrade, shrink, relax, or stretch at least a portion of the fibrotic tissue and being configured to immediately release an effective amount of the antifibrotic agent within 24 hours; and an activator configured to contact the device and cause immediate release of the antifibrotic agent.

The device comprises one or more antifibrotic agents, which degrade or cause the dissolution, shrinkage, relaxation, or stretching of the fibrotic tissue or a portion thereof, such as for example, the shrinkage of fibrotic tissue in or surrounding the tendon sheaths that pass through the carpal tunnel, which reduces pressure in carpal tunnel syndrome.

Antifibrotic agents include, one or more of pancreatic elastase, elastase-2a, elastase-2b, neutrophil elastase, proteinase-3, endogenous vascular elastase, cathepsin G, mast cell chymase, mast cell tryptase, plasmin, thrombin, granzyme B, cathepsin S, cathepsin K, cathepsin L, cathepsin B, cathespin C, cathepsin H, cathepsin F, cathepsin G, cathepsin O, cathepsin R, cathepsin V (cathepsin 12), cathepsin W, calpin 1, calpin 2, chondroitinase ABC, chondroitinase AC, hyaluronidase, chymopapain, chymotrypsin, legumain, cathepsin Z (cathepsin X), cathepsin D, cathepsin E, collagenase, matrix metalloproteinases, such as for example, MMP-1 (collagenase-1), MMP-9, MMP-7 (matrilysin), MMP-8 (collagenase-2), MMP-13 (collagenase-3), MMP-18 (collagenase-4), MMP-2 (gelatinase a), MMP-9 (gelatinase b), MMP-3 (stromelysin-1), MMP-10 (stromelysin-2), MMP-11 (stromelysin-3), MMP-7 (matrilysin), MMP-26 (matrilysin), MMP-12 (metalloelastase), MMP-14 (MT1-MMP), MMP-15 (MT2-MMP), MMP-16 (MT3-MMP), MMP-17 (MT4-MMP), MMP-24 (MT5-MMP) transmembrane, MMP-25 (MT6-MMP), gpl anchor, MMP-19, MMP-20 (enamelysin), MMP-x, MMP-23, MMP-27, MMP-28 (epilysin), ADAMTS-1, ADAMTS-2, ADAMTS-3, ADAMTS-4 (aggrecanase-1), ADAMTS-5(aggrecanase-2), ADAMTS-14, papain, subtilisin, subtilisin A, heparanase. tyrosine kinase inhibitors: imatinib mesylate, dasantinib, nilotinib, inhibitors of PKC-delta and other kinases, TGF-beta receptor inhibitors, HMG-CoA inhibitors, angiotensin inhibitors: angiotensin-converting enzyme inhibitors, angiotensin-II receptor antagonist, pirfenidone, rosiglitazone, cannabinoid receptor, trabedersen, lerdelimumab, metelimumab, mycophenolate mofetil, interferon, or a combination thereof. In some embodiments, the antifibrotic factors include, but are not limited to, interleukins, interferons, cytokines, chemokines, chemotactic molecules, macrophages, lymphocytes, tumor necrosis factor alpha (TNF-alpha), T cells, interferon gamma (IFN-gamma), relaxin, hormones (e.g., progesterone, estrogen, testosterone, growth hormone, thyroid hormone, parathyroid hormone, etc.) or a combination thereof.

In one embodiment, the antifibrotic agent comprises relaxin. Relaxin is a hormone with a number of important functions, which include the modulation of the reproductive physiology of human beings and other mammals, including, but not limited to, maintaining pregnancy, effecting parturition, and enhancing sperm motility as an aid in fertilization.

Relaxin has significant effects on connective tissue, as evidenced by its role in pregnancy, for example on the pubic symphysis and rearrangement of collagenous filaments effecting parturition; depressant effects on the myometrium; preparation of the endometrium for implantation; role in luteolysis; growth and differentiation of the mammary glands; enhancement of sperm motility; and augmentation of the ability of sperm to penetrate the human cervix. Relaxin has been implicated in the dilation of cardiac and blood vessels' smooth muscle cells, and can be used in the treatment of severe chronic pain, particularly pain arising from stretching, swelling, or dislocation of tissues. The drug depot can contain relaxin as the antifibrotic agent and be administered locally to the fibrosis tissue.

In one embodiment, the relaxin comprises human relaxin, where its methods of preparation, including synthesis in recombinant cell culture, are known. Included within the scope of the term "relaxin" are human relaxins from recombinant or native sources as well as relaxin variants, such as amino acid sequence variants. The predominant species of human relaxin in the corpus luteum and serum is the H2 relaxin form with a truncated B chain, i.e., relaxin H2(B29 A24), wherein the four C-terminal amino acids of the B-chain are absent. Also included within the scope of the term "human relaxin" are other insertions, substitutions, or deletions of one or more amino acid residues, glycosylation variants, unglycosylated human relaxin, organic and inorganic salts, covalently modified derivatives of human relaxin, human pre-prorelaxin, and human prorelaxin.

Compounds that can be used as antifibrotic agents are described in Table 3 of U.S. Ser. No. 12/381,063 filed on Mar. 6, 2009 and published as US 2010/0003237, and U.S. Pat. Nos. 7,572,440, 7,132,098. These entire disclosures are hereby incorporated by reference in the present disclosure. Exemplary antifibrotic agents include calpain 1, cathepsin B, cathepsin G, cathepsin L, chondroitinase ABC, chondroitinase AC, chymopapain, chymotrypsin, collagenase, hyaluronidase, MMP-3 (stromelysin-1), MMP-7 (matrilysin), papain, subtilisin, subtilisin A, matrix metalloproteinases or a combination thereof.

In some embodiments of the methods provided herein, the antifibrotic agent is administered in an amount sufficient to maintain a pharmacologically active level of the antifibrotic agent locally at the site of implantation in an amount to degrade, shrink, stretch, or relax at least a portion of the fibrotic tissue or healthy fibrous tissue, which reduces pain and/or inflammation at the site. For example, the antifibrotic agent can be administered in an amount sufficient to maintain a pharmacologically active level of the antifibrotic agent at the site of implantation to degrade at least a portion of the fibrotic tissue or be in the plasma in an amount of, for example, at least or about 5 U/mL, 6 U/mL, 7 U/mL, 8 U/mL, 9 U/mL, 10 U/mL, 15 U/mL, 20 U/mL, 30 U/mL, 40 U/mL, 45 U/mL, 50 U/mL or more. In a particular embodiment of the methods, the antifibrotic agent is administered in an amount sufficient to maintain a pharmacologically active level of the antifibrotic agent at the site of implantation or it can be in the plasma in an amount of at least or about 10 U/mL. In some embodiments, the amount of antifibrotic agent released from the device can be measured by measuring it in tissue or body fluid, such as, for example, blood, cerebral spinal fluid, urine, sweat, semen, plasma or a saliva sample taken from the mammal.

In some embodiments of the methods for treating the fibrotic tissue in which an antifibrotic agent is administered thereto, the antifibrotic agent released from the device is 0.02 mg/kg (of the subject), 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.5 mg/kg, 0.55 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg or more. In one example, the amount of antifibrotic agent administered is 0.05 mg/kg-0.8 mg/kg.

In some embodiments of the methods provided herein, the antifibrotic agent is hyaluronidase. Hyaluronidase is available from various manufactures and is described in U.S. Pat. Nos. 7,767,429; 7,169,405; 7,132,098; 7,572,440; 6,958,149; and U.S. Publication Nos. US20040268425; US20100003238; US20090214505; US20100003237; and WO/2009/111066. The entire disclosures of these patents and publications are herein incorporated by reference in their entirety into the present disclosure. One form of hyaluronidase suitable for use in the device is available from Halozyme Therapeutics, Inc. (Ill. USA), which is a recombinant human hyaluronidase glycoprotein enzyme platform (rHuPH20). The hyaluronidase can be pegylated or a pegylated variant and incorporated into the device (e.g., drug depot).

In some embodiments of the methods provided herein, the hyaluronidase is administered in an amount sufficient to maintain a pharmacologically active level of the hyaluronidase locally at the site of implantation in an amount to degrade at least a portion of the fibrotic tissue, which, in some embodiments, allows the fibrotic tissue to shrink. This will reduce pain and/or inflammation at the site. For example, the hyaluronidase can be administered in an amount sufficient to maintain a pharmacologically active level of the hyaluronidase at the site of implantation to degrade at least a portion of the fibrotic tissue or it can be in the plasma in an amount of, for example, at least or about 5 U/mL, 6 U/mL, 7 U/mL, 8 U/mL, 9 U/mL, 10 U/mL, 15 U/mL, 20 U/mL, 30 U/mL, 40 U/mL, 45 U/mL, 50 U/mL or more. In a particular embodiment of the methods, the hyaluronidase is administered in an amount sufficient to maintain a pharmacologically active level of the hyaluronidase at the site of implantation or it can be in the plasma in an amount of at least or about 10 U/mL.

In some embodiments of the methods for treating fibrosis in which a hyaluronidase is administered thereto, the hyaluronidase released from the device is 0.02 mg/kg (of the subject), 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.5 mg/kg, 0.55 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg or more. In one example, the amount of hyaluronidase administered is 0.05 mg/kg-0.8 mg/kg.

In some embodiments, the device (e.g., drug depot) may comprise hyaluronic acid, hyaluronan, or hyaluronic acid polymers having a MW of 100,000 to 10,000,000.

In some embodiments, the antifibrotic agent, instead of an enzyme, can be an agent that dehydrates the fibrotic tissue, such as for example, a polycationic polymer. Polycationic polymers have a positive charge that interacts with the negatively charged proteins, peptides, or polysaccharides in the fibrotic tissue, which results in the water being displaced through a combination of electrostatic and osmotic mechanisms. With a polycationic polymer, the proteins, peptides, and polysaccharides of the fibrotic tissue are not degraded, but the water is prevented from associating with them, with the result that the fibrotic tissue shrinks.

In some embodiments, the size of the fibrotic tissue is reduced by about 15-20%, 20-25%, 25-30%, 30-35%, 35-40%, 45-50%, 55-60%, 65-70%, 75-80%, 85-90%, or 95-100%.

Some polycationic polymers include, but are not limited to, a polymer of an amino acid, such as D-lysine, L-lysine, D-arginine, L-arginine, D-histidine, or L-histidine or a combination thereof. In some embodiments, the cationic polymer comprises dextran, an arabinogalactan, a pullulan, a cellulose, an inulin, a chitosan, an ornithine polymer, a spermine polymer, a spermidine polymer, or polyethylenimine or a combination thereof. Some cationic polymers are described in US 2007/0258941 (U.S. Ser. No. 11/799,393 filed May 1, 2007). The entire disclosure is herein incorporated by reference into the present disclosure.

In certain embodiments, the cationic polymer is at least about 2 kDa in average size. For example, the polymer is at least about 300 kDa in size. An exemplary polymer is a polylysine, comprising, for example, at least one of D-lysine and L-lysine monomers. Thus the polymer, for example the polylysine, is about 100 kDa to about 300 kDa in size.

For administration of the cationic polymer, the dosage ranges from about 0.0001 to 100 mg/kg, and more usually 0.01 to 5 mg/kg, of the subject body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regimen entails a single administration or administration once per week, once every two weeks, once every three weeks, once every four weeks, once a month, once every 3 months or once every three months to 6 months. Dosage regimens for a cationic compound of the current application include about 1 mg/kg body weight or about 3 mg/kg body weight by a locally administered injection.

In some embodiments, the antifibrotic agent and optionally one or more additional therapeutic agents (e.g., growth factor, analgesic, anti-inflammatory agent, activator, etc.) are included in a device that is a drug depot. A "drug depot" comprises the composition in which at least one therapeutic agent or active pharmaceutical ingredient or drug is administered to the body. Thus, a drug depot may comprise a physical structure to facilitate implantation and retention in a desired site (e.g., a cartilage, bone tissue, site of pain and/or inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent (e.g., antifibrotic agent) for delivery to the site. In various embodiments, the drug depot provides an optimal drug concentration gradient of the therapeutic agent at a distance of up to about 0.1 cm to about 5 cm from the implant site, and comprises at least one therapeutic agent or its pharmaceutically acceptable salt.

The term "therapeutic agent" includes any molecule, protein, growth factor, etc. which would be contemplated for administration in, at or near the fibrotic tissue of a mammal. Such examples would include, but are not limited to one or more antifibrotic agents, growth factors, anti-inflammatory agents (e.g., NSAIDS), antibiotics, analgesics, muscle relaxants, or the like, as well as any molecule or cell, which decreases, blocks, inhibits, abrogates or interferes with the pro-inflammatory cascade of proteins leading to an inflammatory response. For example, a suitable TNF-α antagonist can bind TNF-α, and includes anti-TNF-α antibodies and/or receptor molecules which bind specifically to TNF-α, as well as small molecules which antagonize TNF-α activity. A suitable TNF-α antagonist can also prevent or inhibit TNF-α synthesis and/or TNF-α release. Another example may also provide for any cytokine or biologically active fragment thereof which possesses the ability to decrease, block, inhibit, abrogate or interfere with the pro-inflammatory response promoted by other cytokine proteins (e.g., IL-10, IL-4, IL-13 and TGF-β) as well as any molecule, cell, which positively modulates the anti-inflammatory effect of such an anti-inflammatory cytokine so as to impart an increase in the ability to reduce patient inflammation and/or pain.

The therapeutic agent may comprise growth factors that modulate the growth or differentiation of other cells, particularly connective tissue progenitor cells. The therapeutic agent may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein)or combinations thereof.

In some embodiments, the device comprises an antifibrotic agent and growth factors (e.g., osteogenic protein). Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP, " "osteogenic protein" and "osteogenic factor" embrace the class of proteins typified by human osteogenic protein 1 (hOP-1) and are described in U.S. Pat. No. 7,572,440. The entire disclosure is hereby incorporated by reference in the present disclosure.

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vg1, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily. It is a 139 amino acid residue long homodimer of MW 36,000. OP-1 induces new bone formation in vivo and promotes the repair of diaphyseal segmental bone defects and is described in U.S. Pat. No. 7,132,098. The entire disclosure is hereby incorporated by reference in the present disclosure.

In some embodiments, the therapeutic agent can comprise cells. Suitable cells include, without limitation, mesenchymal stem cells, periosteal cells, pluripotent stem cells, embryonic stem cells, osteoprogentior cells, osteoblasts, osteoclasts, bone marrow-derived cell lines, or any combination thereof. Other therapeutic agents include, for example, DNA, RNA, and their derivatives; vehicles for gene therapy, agents for inducing cell differentiation or de-differentiation or the like.

The therapeutic agent may also comprise nutrients such as chondroitin sulfate and/or glucosamine. The therapeutic agent can also include a lubricant including, but not limited to, lubricin, polyethylene glycol, or any combinations thereof.

In one embodiment, the therapeutic agent in the depot includes an antifibrotic agent, an anti-inflammatory, an anti-apoptotic, a proliferative agent, a fibrosis initiating agent, a differentiating agent, a gene therapy agent, a lubricating agent, a nutrient, an anti-innervating agent, a hygroscopic agent, or a combination thereof.

A depot contains one or more therapeutic agent(s), as discussed above. A "depot" includes but is not limited to capsules, coatings, matrices, wafers, sheets, strips, ribbons, pills, pellets, microspheres, or other pharmaceutical delivery system or a combination thereof. Suitable materials for the depot are ideally pharmaceutically acceptable biodegradable and/or any bioabsorbable materials that are preferably FDA approved or GRAS materials. At least a portion or layer of the depot will, on contact with the activator, immediately release the antifibrotic agent. This may be by, for example, increasing the degradation of the portion or layer of the drug depot, or by increasing the porosity of the drug depot, or by increasing diffusion of the antifibrotic agent out of the drug depot, or by ionic exchange mechanisms.

In some embodiments, the activator will increase dissolution of the depot or layer of the depot by solvent dissolution, or by mechanically, chemically, or thermally degrading the depot or layer of the depot to cause release of the antifibrotic agent. For example, in some embodiments, the activator will cause a mechanical, chemical, or thermal opening or release of a layer or portion of the depot (e.g., opening a "door" with a jet of saline; shrinking a retention layer by chemical exposure, causing it to detach partially; using a temperature change to induce a shape change in retention layer made of a shape-memory polymer, such that the layer detaches partially) to cause release of the antifibrotic agent.

The depot may contain materials that can be polymeric or non-polymeric, as well as synthetic or naturally occurring, or a combination thereof. Typically, the depot will be a solid or semi-solid formulation comprising a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

Suitable drug depots useful in the present application are described in U.S Ser. No. 12,105,474 filed Apr. 18, 2008 and published as U.S. Publication No. 20090263489, and U.S Ser. No. 12/396,122, filed Mar. 2, 2009 and published as US20090263459. The entire disclosure of these applications is incorporated by reference herein in their entirety.

The drug depot may be microspheres or contain microspheres. Microspheres include generally spherical particles about 10 microns to about 2000 microns, or 10 microns to 1000 microns, or 50 microns to 250 microns and at least a population of microspheres in a diameter permitting parenteral administration. The process used to make the microspheres can be controlled to achieve a particular desired size range of microspheres. Other methods, such as sieving, can be used to more tightly control the size range of the microspheres.

In some embodiments, the drug depot comprises microspheres of a size range of from about 100 to 400 microns, which is well suited for delivery to the target tissue sites.

Microspheres comprise a hollow space encapsulated by lipids, polymers, or at least one surfactant, or any combination thereof, wherein the hollow space comprises a therapeutic agent (e.g., antifibrotic agent). In different embodiments, microspheres may include microbubbles or liposomes.

In some embodiments, the microspheres contain the therapeutic agent (e.g., antifibrotic agent) and can comprise a polymer, without limitation, poly(alpha-hydroxy acid), polyhydroxybutyric acid, polycaprolactone, poly(propylene fumarate), PEG, polyorthoester, polyanhydride, polyvinyl alcohol and ethylenevinyl acetate, or the like or combinations or copolymers thereof. In some embodiments, the microsphere can be derived from a poly(alpha-hydroxy acid), in particular, from a poly(lactide) ("PLA") or a copolymer of D,L-lactide and glycolide or glycolic acid, such as a poly(D, L-lactide-co-glycolide) ("PLG" or "PLGA"), or a copolymer of D,L-lactide and caprolactone. The microspheres may be derived from any of various polymeric starting materials which have a variety of molecular weights and, in the case of the copolymers such as PLG, a variety of lactide:glycolide ratios, the selection of which will be largely a matter of choice, depending in part on the desired dose of the active ingredient(s).

In some embodiments, the microspheres containing the antifibrotic agent are loaded into the formulation and are disposed uniformly throughout it or in a particular region (e.g., center or borders) and delivered in, at, or near the fibrosis tissue. The microspheres will degrade and release the therapeutic agent at, near or in the fibrotic tissue and the microspheres will begin releasing the therapeutic agent immediately and/or in a sustained release fashion to the desired tissue location.

The drug depot comprises a therapeutically effective amount of the therapeutic agent. A "therapeutically effective amount" or "effective amount" is such that when administered, the drug results in alteration of the biological activity, such as, for example, inhibition of inflammation, reduction or alleviation of pain, improvement in the condition through muscle relaxation, degradation of a portion of the fibrotic tissue, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In one embodiment, the therapeutic agent can be in the depot and used in an amount typically ranging between about 0.1 to 5000 mcg/kg of body weight or about 1 to 1000 mcg/kg of body weight or about 10 to 500 mcg/kg of body weight or about 50 to 250 mcg/kg of body weight.

In some embodiments the formulation of the drug depot is designed for immediate release upon contact with an activator. In other embodiments the formulation is designed for sustained release. In other embodiments, the formulation comprises one or more immediate release surfaces or layers and one or more sustain release surfaces or layers in one depot.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents (e.g., antifibrotic agents) over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, pellets, microparticles, microspheres, microcapsules, spheroids, shaped derivatives or pastes. Further, the formulations may be used in conjunction with any implantable, or insertable system that a person of ordinary skill would appreciate as useful in connection with embodiments herein including but not limited to parenteral formulations, microspheres, microcapsules, pastes, implantable rods, pellets, plates or fibers, etc. The antifibrotic agent can be in the device as a sustained release formulation, where one or more regions or layers of the device release the antifibrotic agent into the fibrotic tissue to degrade the fibrotic tissue over an extended period of time (e.g., 3 months to 1 year).

The immediate release therapeutic agent can be released first. The phrase "immediate release" is used herein to refer to one or more therapeutic agent(s) that is introduced into the body and that is allowed to dissolve in or become absorbed at the location to which it is administered, in part, on contact with an activator. Immediate release refers to the release of drug within a short time period following administration, e.g., generally within a few seconds or minutes or 30 minutes to about 1, 2, 3, 4, 5, 6, 7, 8, 9, 10, 11, 12 hours or within 24 hours after implantation. The antifibrotic agent can be in the device as an immediate release formulation, where one or more regions or layers of the device release the antifibrotic agent into the fibrotic tissue to degrade it over time or when the device contacts an activator. The immediate release region or layer of the device and/or activator can be in liquid solutions, suspensions, or emulsions forms or semi-solid or solid forms having a suitable excipient for immediate release. Suitable excipients are, for example, water, saline, dextrose, glycerol, ethanol, pH buffering agents, metal ion salts, or other such buffers. The formulation also may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, cyclodextrins or a combination thereof.

For example, an immediate release formulation of an antifibrotic agent that can be incorporated into a drug depot can be hyaluronidase formulated with one or more of EDTA, NaCl, $CaCl_2$, histidine, lactose, albumin, Pluronic® F68, TWEEN® and/or other detergent or other similar agents. For example, compositions provided herein can contain one or more pH buffers (such as, for example, histidine, phosphate, or other buffers), or acidic buffer (such as acetate, citrate, pyruvate, Gly-HCl, succinate, lactate, maleate or other buffers), tonicity modifier (such as, for example, an amino acid, polyalcohol, NaCl, trehalose, other salts and/or sugars), stabilizer, chelating agent, such as ethylenediaminetetraacetic acid, ethylenediaminetetraacetate or calcium EDTA, oxygen scavenger, such as methionine, ascorbic acid/ascorbate, citric acid/citrate, or albumin, and/or a preservative, such as preservative containing an aromatic ring (e.g. phenol or cresol). In some embodiments, the depot does not contain any preservatives and, therefore, is preservative free.

Exemplary stabilizers that are useful for the depot containing the antifibrotic agent include, for example, polysorbates or proteins such as human serum albumin. Exemplary concentrations of serum albumin that are useful in the compositions herein include 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL or 1 mg/mL, but can be more or less. Polysorbates also can be present in the depot at, for example, concentrations of or about 0.001%, 0.002%, 0.003%, 0.004%, 0.005%, 0.006%, 00.007%, 0.008%, 0.009%, 0.01%, 0.02%, 0.03%, 0.04%, 0.05%, 0.06%, 0.07%, 0.08%, 0.09% or 0.1%. A metal chelating agent, such as calcium EDTA (CaEDTA), also can be present, such as for example, at concentrations of between approximately 0.02 mM to 20 mM, such as 0.02 mM, 0.04 mM, 0.06 mM, 0.08 mM, 0.1 mM, 0.2 mM, 0.3 mM, 0.4 mM, 0.5 mM, 0.6 mM, 0.7 mM, 0.8 mM, 0.9 mM, 1 mM, 5 mM, 10 mM, 15 mM, 20 mM or more. The pH and the osmolarity of the depot can be adjusted to optimize the conditions for the desired activity and stability of the overall composition. In some embodiments, the compositions provided herein have an osmolarity of at or about 100 mOsm/kg, 120 mOsm/kg, 140 mOsm/kg, 160 mOsm/kg, 180 mOsm/kg, 200 mOsm/kg, 220 mOsm/kg, 240 mOsm/kg, 260 mOsm/kg, 280 mOsm/kg, 300 mOsm/kg, 320 mOsm/kg, 340 mOsm/kg, 360 mOsm/kg, 380 mOsm/kg, 400 mOsm/kg, 420 mOsm/kg, 440 mOsm/kg, 460 mOsm/kg, 500 or more mOsm/kg, and a pH of at or about 6, 6.2, 6.4, 6.6, 6.8, 7, 7.2, 7.4, 7.6, 7.8 or 8.

Generally NaCl can be provided in formulations herein, for example, in an amount that is or is about 100 mM-150 mM or more. For example, an exemplary formulation can contain at or about 10 mM histidine and/or at or about 130 mM NaCl. Other formulations can contain in addition or alternatively lactose, for example, at or about 13 mg/ml. Additionally, an anti-bacterial or anti-fungal agent, including, but not limited to thiomersal, can be present in the formulation. Formulations can further contain Albumin, Pluronic ® F68, TWEEN ® and/or other detergent. The formulations are provided at a pH that is or is about 6.0, 6.1., 6.2, 6.3, 6.4, 6.5, 6.6, 6.7, 6.8, 6.9, 7.0, 7.1, 7.2, 7.3 or 7.4, generally that is or is about pH 6.5. In some embodiments, the drug depot containing the antifibrotic agent is designed for local administration into the fibrotic tissue.

The depot can be designed to provide the desired release rate profile for immediate release and/or sustained release of the therapeutic agent (e.g., antifibrotic agent, analgesic, anti-inflammatory agent, growth factor, etc.). The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least one antifibrotic agent, analgesic, anti-inflammatory agent, growth factor, and/or analgesic agent in a bolus dose on contact with the activator and at least one antifibrotic agent, analgesic, anti-inflammatory agent, and/or growth factor over an extended period of time (e.g., 3 days to 3 months).

The depot can be biodegradable. The term "biodegradable" includes that all or parts of the drug depot will degrade over time by the action of enzymes, by hydrolytic action, triggers (such as an activator) and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In some embodiments, the 50%, 55%, 60%, 65%, 70%, 75%, 80%, 90%, 95%, or 100% of the polymer remains in the depot after one year and after the drug is released from the depot.

The depot may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyetherurethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this application, appear to be non-resorbable over the time frame of the use of the material for this invention.

The drug depot can provide the appropriate pain management medication. The phrase "pain management medication" includes one or more therapeutic agents that are administered to prevent, alleviate or remove pain entirely. These include anti-inflammatory agents, analgesics, anesthetics, narcotics, and so forth, or combinations thereof.

In various embodiments, the depot can be designed to cause an initial burst dose of one or more therapeutic agents within the first 24 hours after implantation or when it is contacted with an activator. "Initial burst" or "burst effect" or "bolus dose" or "pulse dose" refer to the release of therapeutic agent from the depot during the first 24 hours after the depot comes in contact with an activator and/or aqueous fluid (e.g., synovial fluid, blood, plasma, etc.). The burst effect may be an immediate release. The "burst effect" is believed to be due to the increased release of therapeutic agent from the depot on contact with an activator or on contact with a bodily fluid. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region of the depot or individual depot, in various embodiments, can be designed so that a larger initial dose may be released over a short period of time to achieve the desired effect. For example, if a drug depot is designed to release 15 mg of antifibrotic agent per 48 hours, then the initial burst dose or bolus dose region or depot will be designed to release a percentage of the dose within the first 24 hours when it contacts an activator or bodily fluid (e.g., 10 mg of antifibrotic agent or 66% of the 48 hour dose within 24 hours). Thus, the burst effect of the drug depot or region of the drug depot releases more therapeutic agent than the sustained release region or depot.

A region or depot that utilizes a burst effect or bolus dose will release more therapeutic agent (e.g., antifibrotic agent, analgesic, anti-inflammatory, and/or growth factor) than the sustained release region or depot. For example, particularly with painful conditions such as discogenic back pain, or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the susceptibility to the activator, water immiscibility of the solvent, polymer/solvent ratio, and/or the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents and/or activators that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids and/or the activator dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers and/or activators. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst, activator susceptibility, and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

The drug depot may comprise at least one analgesic agent or its pharmaceutically acceptable salt. Examples of analgesic agents include but are not limited to acetaminophen, a local anesthetic, such as for example, lidocaine, bupivacaine, ropivacaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, prophepazine, promedol, properidine, propoxyphene, sufentanil, tilidine, tramadol or a combination thereof. Analgesic agents also include those with analgesic and anti-inflammatory properties, such as, for example, amitriptyline, carbamazepine, gabapentin, pregabalin, clonidine, or a combination thereof.

In some embodiments, the drug depot contains anti-inflammatory agents and/or analgesic comprising flurbiprofen, indoprofen, naproxol, pentazocine, proxazole, tramadol, verilopam, volazocine, xylazine, zucapsaicin, phenyhydantoin, phenobarbital, primidone, ethosuximide, methsuximide, phensuximide, trimethadione, diazepam, benzodiazepines, phenacemide, pheneturide, acetazolamide, sulthiame, bromide, nalorphine, naloxone, naltrexone, salycilates, phenylbutazone, indomethacin, phenacetin, dextropropoxyphene, levomethadyl, pethidine, remifentanil, flupirtine or a combination thereof.

In some embodiments, the anti-inflammatory and/or analgesic agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

The drug depot can comprise at least one analgesic agent or its pharmaceutically acceptable salt and/or at least one anti-inflammatory agent or its pharmaceutically acceptable salt and may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one antifibrotic agent, the at least one analgesic agent or its pharmaceutically acceptable salt or the at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered or in the depot with the antifibrotic agent, anti-inflammatory agent or analgesic agent include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use in the depot include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

For each of the antifibrotic agents, analgesic agents, anti-inflammatory agents and/or growth factor, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or 30 days, or 60 days or 90 days or longer.

The drug depot may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation of the drug depot can occur either at the surface (heterogeneous or surface erosion) or uniformly throughout the drug depot (homogeneous or bulk erosion).

In various embodiments, the depot may comprise a bioabsorbable, and/or a biodegradable biopolymer that may provide immediate release, or sustained release of the at least one antifibrotic agent, at least one analgesic agent, at least one anti-inflammatory agent, and/or at least one growth factor. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, poly(propylene fumarate), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, D,L-lactide-$\epsilon$-caprolactone, D,L-lactide-glycolide-$\epsilon$-caprolactone, poly(glycolide-$\epsilon$-caprolactone), $\epsilon$-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations or copolymers thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dl/g.

In various embodiments, the molecular weight of the polymer in the device can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the therapeutic agent are the only components of the pharmaceutical formulation that is used to make the depot.

In some embodiments, at least 75% of the particles in the depot have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the fibrotic tissue, in various embodiments, the depot may comprise sterile preservative free material.

The depot can be different sizes, shapes and configurations, such as for example, strip, rod, sheet, mesh, pellet, microsphere, sphere, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

In some embodiments, the drug depot (e.g., microspheres, nano spheres, pellets, etc.) can be mixed, stirred, agitated, injected, emulsified, molded, etc. into the formulation to provide a uniform distribution of the drug depot within the formulation. In alternative embodiments, the drug depot (e.g., microspheres, nanospheres, pellets, etc.) can be mixed, stirred, agitated, injected, molded, etc. in the formulation to provide a non-uniform distribution of the drug depot within the formulation in the center or at certain regions of it.

Fibrosis

In one embodiment, a device is provided for treating fibrous tissue in a patient in need of such treatment, the device being biodegradable and implantable at, near, or in a fibrous tissue (normal or abnormal fibrous tissue), the device comprising an antifibrotic agent to degrade, shrink, relax and/or stretch at least a portion of the fibrous tissue and being configured to immediately release an effective amount of the antifibrotic agent within 24 hours and configured to provide sustained release of the antifibrotic agent over a period of up to one year to treat the fibrous tissue. For example, the antifibrotic agent can relax a ligament, which may reduce pain and/or inflammation locally in the area.

In another embodiment, there is a method for treating fibrosis in a patient in need of such treatment, the method comprising administering an implantable and biodegradable device at, near, or in a fibrotic tissue, the device comprising an antifibrotic agent to degrade, shrink, relax, or stretch at least a portion of the fibrotic tissue and being configured to immediately release an effective amount of the antifibrotic agent within 24 hours on contact with an activator and administering the activator at, near, or in the fibrotic tissue so as to cause immediate release of the antifibrotic agent from the device.

In yet another embodiment, there is a method for treating fibrosis, the method comprising administering an implantable and biodegradable device to the fibrotic tissue, the device comprising a antifibrotic agent to degrade, shrink, relax, or stretch at least a portion of the fibrotic tissue and being configured to immediately release an effective amount of the antifibrotic agent within 24 hours and to provide sustained release of the antifibrotic agent over a period of up to one year to treat the fibrotic tissue.

A skilled artisan will be capable of determining the desired amount of antifibrotic agent based on a number of factors, including, for example, the degree of fibrosis, the age, weight, and health of the patient. Additionally, the methods provided herein may be used to slow the rate of progression of the fibrosis.

In some embodiments, fibrosis includes any pathological condition resulting from an overproduction or aberrant production of fibrous tissue. Fibrosis may occur in any organ including, for example, kidney, lung, liver, skin, central nervous system, bone, bone marrow, cardiovascular system, an endocrine organ or the gastrointestinal system. Fibrosis includes those disorders or disease states that are caused by or accompanied by the abnormal deposition of scar tissue, or by excessive accumulation of primarily collagenous connective tissue.

Examples of pathologic and excessive fibrotic accumulations include, but are not limited to, pulmonary fibrosis, asthma, adult respiratory distress syndrome (ARDS), chronic obstructive pulmonary disease (COPD), idiopathic pulmonary fibrosis (IPF), acute lung injury (ALI), pulmonary fibrosis due to infectious or toxic agents, such as radiation therapy or chemotherapy, pulmonary fibrosis due to particle inhalation, post-transplant pulmonary fibrosis, perirenal fascitis, glomerulonephritis (GN), diabetic nephropathy, renal interstitial fibrosis, renal fibrosis resulting from complications of drug exposure, HIV-associated nephropathy, transplant necropathy, retroperitoneal fibrosis, perivascular fibrosis in Systemic Lupus Erythematosus (SLE), obstruction-induced fibrosis in kidneys or spleen, benign prostate hypertrophy, fibrocystic breast disease, uterine fibroids, ovarian cysts, endometriosis, coronary infarcts, myocardial fibrosis, cerebral infarcts, congestive heart failure, dilated cardiomyopathy, myocarditis, myelofibrosis, vascular stenosis, progressive systemic sclerosis, polymyositis, scleroderma (which affects the skin and the lungs), dermatomyositis, Raynaud's syndrome, retroperitoneal fibrosis, progressive massive fibrosis, nephrogenic systemic fibrosis, Crohn's disease, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, rheumatoid arthritis, musculoskeletal fibrosis, post-surgical adhesions, liver fibrosis, autoimmune hepatitis, cirrhosis including primary biliary cirrhosis, viral hepatitis including HIV- or Hepatitis C-induced hepatitis, real fibrotic disease, fibrotic vascular disease, e.g., atherosclerosis, varix, or varicose veins, scleroderma, Alzheimer's disease, diabetic retinopathy, glaucoma, proliferative vitreoretinopathy, fibrosis associated with ocular surgery, chronic transplant rejection, graft vs. host disease, radiation-induced fibrosis, and excessive or hypertrophic scar and/or keloid formation in the dermis occurring during wound healing resulting from trauma or surgical wounds.

Fibrosis also includes healthy or normal production of fibrous tissue. In some embodiments, the antifibrotic agent will stretch or relax fibrous tissue (e.g., healthy or normal fibrous tissue, such as muscles, cartilage, tendons, ligaments, etc.) anywhere in the body. For example, in carpal tunnel syndrome, in some embodiments, the flexor retinaculum generally has normal amounts of fibrous tissue. However, it is beneficial to degrade this normal fibrous tissue so the flexor retinaculum can stretch more easily to accommodate the excess tissue within the carpal tunnel. In some embodiments, the antifibrotic agent can degrade, stretch, and/or relax the normal fibrous tissue, which can be beneficial in treatment of conditions such as scoliosis, tarsal tunnel syndrome, carpal tunnel syndrome and other conditions, where degrading, stretching and/or relaxing healthy or normal fibrosis tissue would be beneficial.

In one embodiment, the disorder to be treated is a disorder that results in fibrosis or sclerosis, including but not limited to groups of disorders selected from skeletal muscle fibrosis, irradiation-induced fibrosis, autoimmune-related fibrosis, cardiovascular fibrosis, arteriosclerotic disorders, pulmonary fibrosis, adult respiratory distress syndrome, inflammatory disorders, scleroderma, cirrhosis, keloids, adhesions, hypertrophic scars; skeletal muscle fibrosis associated with a condition, such as muscular dystrophy, denervation atrophy induced by neuromuscular disease, or traumatic injury-induced denervation atrophy; cardiovascular fibrosis selected from left ventricular hypertrophy secondary to hypertension, fibrosis associated with myocardial infarction, fibrosis associated with ischemiareperfusion injury, or fibrosis associated with myocarditis; dermal fibrosis, keloid formation, hypertrophic scar formation, or adhesion formation; pulmonary fibrosis, pulmonary fibrosis due to adult respiratory distress syndrome and irradiation induced fibrosis, or a combination thereof.

In some embodiments, the fibrosis is a localized type of fibrosis, such as for example, stenosing tenosynovitis (trigger finger), Dupuytren's disease (palmar fibromatosis), Ledderhose's disease (plantar fibromatosis), Peyronie's disease, fibromatosis colli, keloids, mediastinal fibrosis, carpal tunnel syndrome, tarsal tunnel syndrome or a combination thereof.

In some embodiments, the device having the antifibrotic agent in it is implanted in, at or near fibrotic tissue to treat carpal tunnel syndrome. Carpal tunnel syndrome is a progressive condition caused by compression of the median nerve due to local fibrosis and/or swelling.

Typically, carpal tunnel syndrome is the group of symptoms that result from pinching the medial nerve in the wrist. These symptoms range from numbness in a few fingers to pain in forearms, hands, or even shoulders. The first symptom most people notice is numbness in the three middle fingers when they first wake up. Failure to reduce the pinching of medial nerve can result in loss of hand use.

The carpal tunnel is the interior of the wrist through which the medial nerve, tendons, and blood vessels pass. Three sides of the carpal tunnel are bone. The other side is a sheath, and the flexor retinaculum, which is made of ligament material. By implanting the device in, at or near the fibrotic tissue, this decreases fibrosis and relaxes the flexor retinaculum in carpal tunnel syndrome.

In some embodiments, the device having the antifibrotic agent in it is implanted in, at or near fibrotic tissue to treat tarsal tunnel syndrome. Tarsal tunnel syndrome is a progressive condition caused by compression of the posterior tibial nerve and/or the medial and lateral plantar nerves due to local fibrosis and/or swelling. By implanting the device in, at or near the fibrotic tissue, this decreases fibrosis and relaxes the flexor retinaculum in tarsal tunnel syndrome.

The depot containing the antifibrotic agent and/or activator can be incorporated in a syringe or cannula and delivered to the fibrotic tissue. The depot containing the antifibrotic agent and/or activator may be delivered to the fibrotic tissue locally in a variety of forms, such as beads, fibers, flakes, granules, microspheres, nano-particles, particles, pellets, platelets, powder, randomly shaped particles, rods, chunks, pieces, and so forth.

In some embodiments, whatever form the drug depot is in, it may be delivered to the fibrotic tissue, for example, utilizing "dry" or "wet" delivery methods.

In the "wet" delivery method, the depot containing the antifibrotic agent may be fluidized, for example, by mixing the depot containing with a medium to form a gel, suspension, paste, solution, mixture, etc. of the antifibrotic agent that is sufficiently fluid to be delivered through a needle, catheter, trocar, cannula, syringe, caulk gun-like device, barrel-plunger device, other injection or extrusion devices, or any other such applicable delivery device. For example, the delivery device may be used to pierce or puncture the fibrous tissue. If desired, a more rigid, larger diameter cannula may be used to gain access to the tissue surrounding the fibrotic tissue, and a smaller diameter needle may be used to inject the drug depot at the desired target tissue site. Additionally, if desired, a more rigid instrument such as a stylet may be used to guide the delivery device through the body and towards the desired location.

In some embodiments, the drug depot may be introduced into the delivery device and subjected to pressure or mechanical forces in order to force the drug depot to exit the distal end of the delivery device and enter the fibrotic tissue. In an exemplary embodiment, a syringe filled with the drug depot in the form of a gel, suspension, paste, solution, mixture, etc. may be used to force the drug depot through the delivery device (e.g., a needle, cannula, catheter, trocar, etc.) and into the target tissue site (bone, muscle, tendon, ligament, blood vessel, etc.), where the therapeutic agent will be released from the drug depot and degrade, shrink, relax, or stretch the fibrotic tissue.

In some embodiments, the drug depot may be delivered to the fibrotic tissue via a "dry" delivery method, without rendering the drug depot flowable. According to the dry delivery method, the drug depot may be packed into a small diameter delivery device such as a needle, catheter, trocar, cannula, etc. in the form of a dry powder, particulates, small chunks, pellets, short rods, chunks, pieces, and so forth. No fluid is mixed with the drug depot prior to delivery to the fibrotic tissue. In some embodiments, the delivery device has a diameter of no more than about 3 mm, 2 mm, or 1 mm.

In some embodiments, the fibrotic tissue may be punctured and the delivery device inserted. In some embodiments, the delivery device itself may be used to puncture the fibrotic tissue, especially when the delivery device is a needle or trocar. The distal end of the delivery device then may be brought closer to the target tissue site. A plunger, stylet, or other such device may be used to extrude or push the drug depot through the delivery device and into the target tissue site. When the one or more drug depots are delivered to the target tissue site, the delivery device may be removed.

Activators

The device (e.g., drug depot) can be activated to allow immediate release of the antifibrotic agent from the device by exposure, either directly or indirectly, to an activator. The activator may be part of the device (e.g., a layer that is pierced after implantation) or separate from the device or a combination thereof. The activator may be in liquid form (e.g. solution or suspension), solid or semisolid form that is administered in the same way the device (e.g., drug depot) is administered—that is locally to the fibrotic tissue so as to contact the device and cause release of the antifibrotic agent from it.

The activator can be a molecule that increases the release of the antifibrotic agent from the device. Upon in vivo administration, temporal activation of the device is achieved by exposure (prior to or upon administration subsequently, intermittently or simultaneously) to one or more specific activators that provide an activating condition sufficient for activation of the device and release of the antifibrotic agent from the device. For example, activation can be achieved by exposure of the device to, for example, a liquid at a certain temperature (e.g. heat or cold), pH, salt concentration, and/or metal ions (e.g., $Ca^{2+}$) concentration. The activator may contain sufficient concentrations of reducing agents or oxidizing agents for activation of the device and/or antifibrotic agent. The choice of activator will vary depending upon the choice of the antifibrotic agent and the device used. Generally, an amount (e.g. concentration, level or degree) of activator sufficient to generate and activate the depot is used. This amount can be readily determined empirically and is dependent upon the selected device and antifibrotic agent used.

Initially, activating conditions are not normally present, endogenously, in sufficient amounts for activation of device and/or antifibrotic agent in vivo. For example, the pH of the synovial fluid can be from about 5.7 to about 7.5. Therefore, one can administer an activator that has a lower or higher pH so that the activator contacts the device and causes controlled release of the antifibrotic agent in the specific target area because the lower or higher pH condition is not normally present. In another example, the physiological level of metal ions, such as calcium, in the fibrotic tissue are far lower than the effective amounts required for activation of the device. Thus, the device can be designed to increase release of the antifibrotic agent as the concentration of metal ions increases by administering an activator containing metal ions.

The amount of time the device (e.g., drug depot) is activated can be for a predetermined time to cause immediate release of the antifibrotic agent. For example, an activator can be provided containing an amount of activating condition, such as the concentration, effective amount, level or degree, which is chosen such that the antifibrotic agent is released from the device for a set time under the environment and conditions it is exposed to upon in vivo administration. In one example, where acidic pH is the activating condition, the buffering capacity of an acidic buffer activator can be adjusted to modulate the time of its resistance to changes in pH. The predetermined time at which an activator activates the device can be determined empirically and is a function of the disease to be treated, the individual treated, the choice of antifibrotic agent and the choice of the activator. A device can be active following in vivo administration in the presence of an activator for at or about 1 minute, 2 minutes, 3 minutes, 4 minutes, 5 minutes, 10 minutes, 20 minutes, 30 minutes, 40 minutes, 50 minutes, 1 hour, 2 hours, 3 hours, 4 hours, 5 hours, 6 hours or more.

In some embodiments, not only is the device activated by the activator, but the antifibrotic agent (e.g., an enzyme) can be activated by the activator as well. For example, pH may be at a sufficient level to not only activate release of the enzyme from the depot, but also activate the enzyme itself. Such methods take advantage of proteins having enzymatic activity only at acidic pH, while remaining inactive or becoming unstable and degraded at neutral pH (7.0) or basic pHs. Hence, it is contemplated herein that the antifibrotic agent can be an enzyme that can exhibit activity at acidic conditions, but is substantially inactive at neutral pH. A substantially active enzyme is any exhibiting 70% or more activity of the enzyme at its pH optima, for example, at or about 75%, 80%, 85%, 90%, 95%, 98%, 99%, 99.5% or 100% of activity as present at the enzyme's pH optima. One of ordinary skill in the art knows or can determine the pH optima of an enzyme and can assess activity differences at varying pH conditions. For example, the pH optima of cathepsin L is or is about 5.5, but can vary within a range of 4.5 to 6 depending on the particular species of cathepsin L, buffer condition or ionic strength. Cathepsin L is substantially inactive at or above pH 7.4. It will be understood that the pH optima can be different depending on the substrate used, buffer conditions, ionic strength and species of enzyme. Thus, reference to pH optima herein is for exemplification only. One of ordinary skill in the art can empirically determine the pH optima of an enzyme under specific conditions. For example, buffer conditions and ionic strengths can be varied to determine an enzymes activity under various pH conditions.

Thus, the ability to activate the device and/or the antifibrotic agent by administration before, during, or after an activating agent that is not normally present at the site of administration permits the temporal regulation of the device and/or the antifibrotic agent in the fibrotic tissue. For example, when the pH is rendered acidic, such as for example, by addition of an enzyme such as a lysosomal enzymes or buffered acid solution, the device will immediately release the antifibrotic agent and the antifibrotic agent will be activated until the pH becomes more neutral or basic, then the release and the activity of antifibrotic agent will decrease or stop.

In one embodiment, the activator, when administered, temporarily lowers the pH of the fibrotic tissue to less than or about 3.0, 3.5, 4.0, 4.5, 5.0, 5.5, 6.0 or 6.5 such that the device immediately releases the antifibrotic agent and this pH will also activate the antifibrotic agent (e.g., hyaluronidase). Acidic activators can be an acidic buffer solution that is organic or inorganic acid. Generally, the acidic activator can be a liquid solution that can be a weak acid. Exemplary acids include, but are not limited to, 2-(N-morpholino)ethanesulfonic acid) (MES), acetic acid, citric acid, succinic acid, lactic acid, maleic acid, glycine-hydrochloric acid, citric phosphate and histidine, formate, glycine, malate, MES, phosphate, piperazine, propionate, pyridine and succinate or the like. In some embodiments, the activator can be a base an increase the pH of the environment surrounding the fibrotic tissue to more than or about 6.0, 6.5, 7.0, 7.5, 8.0, 8.5, or 9.0 such that the device immediately releases the antifibrotic agent and this pH will also activate the antifibrotic agent (e.g., hyaluronidase).

Suitable activators are, for example, enzymes (e.g., lysosomal enzymes, etc.) water, saline, dextrose, glycerol or ethanol, pH buffering agents, reducing or oxidizing agents, metal ion salts, or other such buffers, hypotonic or hypertonic solutions (e.g., dextrose, saline, etc.), phosphate buffered saline (PBS), lactated ringers, sodium acetate, sorbitan monolaurate, triethanolamine oleate and cyclodextrins, glucose, polyethylene glycol, polypropylene glycol, sodium hydroxide, hydrochloric acid, citric acid or lactic acid for pH adjustment or combinations thereof.

In some embodiments, the activator can comprise a metal cation (e.g., $Ca^{2+}$, $Mg^{2+}$ or $Zn^{2+}$). The metal ion can be provided in the form of an aqueous composition, for example, as a calcium salt. The metal cation can be in a layer in the device or it can be separate from the device. If provided as a separate composition from the device, it can be in the form of a concentrated liquid or in lyophilized or powdered form, addition of the metal ion to the device will result in an activated device that can immediately release the antifibrotic agent.

Generally, activation is achieved by exposing a device and/or an inactive enzyme to a metal cation at a concentration sufficient for activation. Precise amounts can be empirically determined or are known to those of ordinary skill in the art. For example, in vitro activation may require 10-50 or 300-500 micro molar calcium concentrations. Typically, for purposes herein, activatable amounts to activate the device include those that require sufficient concentration of a metal ion for activation at a concentration that exceeds the physiological level of metal ion present in the fibrotic tissue.

In some embodiments, the activation of the device by the metal ion can be controlled by a chelating agent, such as for example, ethylenediaminetetraacetic acid (EDTA) or ethylene glycol tetraacetic acid (EGTA) (concentrations from about 5 to about 100 mM or higher depending on the application) to tie up any metal ion to prevent triggering the activation reaction until desired. The activation reaction then can be triggered by adding the metal ion at a concentration sufficient to overcome the effects of the chelator. Precise amounts can be empirically determined. As the metal ion is consumed by the antifibrotic agent, the release from the device will decrease or stop.

In some embodiments, the activator can comprise a reducing agent, such as for example, a thiol or non-thiol reducing agent (e.g., tris(2-carboxyethyl)phosphine (TCEP) or cysteine. The reducing agent can be provided in the form of a liquid or in lyophilized or powdered form and addition of the reducing agent to the device and/or antifibrotic agent will result in an activated enzyme. For example, to activate cathepsin L, the antifibrotic agent, generally requires 1-50 mM cysteine. Typically, for purposes herein, reducing agents that can activate the device and/or antifibrotic agent include those that require sufficient concentrations of a reducing agent for activation at a concentration that exceeds the physiological level of reducing agent present in the fibrotic tissue. The reducing agent can be added prior to, simultaneously, subsequently or intermittently upon administration of the device.

In some embodiments, the activator can comprise a liquid at a certain temperature that causes release of the antifibrotic agent from the device to proteolytically degrade at least a portion of the fibrotic tissue. The liquid activator can be at a temperature that is lower than the physiological temperature (e.g. 37° C.). For example, the liquid activator (e.g., saline, dextrose, glycerol, ethanol, PBS, lactated ringers, etc.) may be heated or cooled to be at a temperature of about 20° C., 21° C., 22° C., 23° C., 24° C., 25° C., 26° C., 27° C., 28° C., 29° C., or 30° C.) when it contacts the device, which will cause the release of the antifibrotic agent. As the temperature of the liquid approaches physiological temperature, the device may stop the immediate release or reduce the immediate release of the antifibrotic agent. In some embodiments, the antifibrotic agent may be completely released from the depot as the liquid approaches physiological temperature.

In some embodiments, the activator can comprise a liquid activator that can be at a temperature that is higher than the physiological temperature (e.g. 37° C.). For example, the liquid activator (e.g., saline, dextrose, glycerol, ethanol, PBS, lactated ringers, etc.) may be heated or cooled to be at a temperature of about 37.5° C., 38° C., 38.5° C., 39° C., 39.5° C., or 40° C., 45° C., 50° C., 55° C., 60° C., 65° C., 70° C., 75° C., 80° C., 85° C., or 90° C., when it contacts the device, which will cause the release of the antifibrotic agent. As the temperature of the liquid approaches physiological temperature, the device may stop the immediate release or reduce the immediate release of the antifibrotic agent. The duration of exposure to the activator can be continuous, can be for a predetermined time, or can be intermittent. Thus, the time period permitting activation is flexible and can be adapted to the particular device and/or antifibrotic agent that is used.

As the temperature of the device approaches the physiological temperature, in some embodiments, the device may reduce or stop the immediate release of the antifibrotic agent by about 70%, 75%, 80%, 85%, 90%, 95%, 99%, 99.5%, or 100%.

In some embodiments, the activator takes advantage of the requirement for exogenous activating conditions, which cause immediate release of the antifibrotic agent for a limited duration during use, such as upon in vivo administration of the activator to the body.

In some embodiments, after the activator has exerted its effect on the immediate release layer of the device, the device will then degrade and provide sustained release of the antifibrotic agent over time.

In some embodiments, the activator can be energy (kinetic, potential, thermal, gravitational, sound, elastic and/or electromagnetic energy) that is applied to the device or externally to the device (e.g., skin or tissue that surrounds the device) and causes immediate release or sustained release of the therapeutic agent. For example, the activator can be a wireless or wired electrical signal, electromagnetic radiation, magnetic field, acoustic energy, or ultrasonic energy. When it comes in contact either directly or indirectly with the device (e.g., drug depot) the activator will cause release of the therapeutic agent.

For example, ultrasonic energy can be applied to the area (skin, tissue, wound site, etc.) that the drug depot is implanted and without wishing to be bound by any particular theory, ultrasonic energy is propagated into the area (e.g., tissue), the wave energy is converted into heat because tissue can absorb energy to produce heat, causing release of the antifibrotic agent from the temperature sensitive depot. Ultrasound also causes tissues to vibrate, which may cause the depot or layer of the depot to rupture and release the antifibrotic agent. In some embodiments, the ultrasonic energy is applied at a frequency between 1 kHz and 10 MHz.

The device may comprise shape memory polymers (SMPs) and shape memory alloys (SMAs). SMPs are polymers derive their name from their inherent ability to return to their original "memorized" shape after undergoing a shape deformation. SMPs that have been formed into a depot or layer of the depot can be deformed to any desired shape below or above its glass transition temperature (Tg) to cause release of the antifibrotic agent.

Some polymers that can exhibit shape memory properties include, but are not limited to, polyurethane, crosslinking polyethylene homopolymer, styrene-butadiene thermoplastic copolymer systems, polyisoprene, copolymers of stearyl acrylate and acrylic acid or methyl acrylate, polymers formed of norbornene or dimethaneoctahydronapthalene homopolymers or copolymers, set forth in U.S. Pat. No. 4,831,094. Additionally, styrene copolymer based SMPs are disclosed in U.S. Pat. Nos. 6,759,481 and 6,720,402 which are incorporated herein by reference.

Preferred shape memory polymers include, but are not limited to, polyurethanes, polynorbornene, styrene-butadiene copolymers, and cross-linked polyethylene. polyacrylates, polyamides, polysiloxanes, polyethers, polyether amides, polyureas, polyether esters, urethane/butadiene copolymers, block copolymers of polyethylene terephthalate (PET) and polyethyleneoxide (PEO), block copolymers containing polystyrene and poly(1,4-butadiene), an ABA triblock copolymer made from poly(2-methyl-2-oxazoline) and polytetrahydrofuran, polyhedral oligosilsesquioxane, PEO-PET block copolymers, AA/MAA copolymer, MAA/N-vinyl-2-pyrrolidone, PMMA/N-vinyl-2-pyrrolidone, or a combination thereof.

The shape memory polymers can be a light activated shape memory polymer (LASMP), which use processes of photo-crosslinking and photo-cleaving to change Tg. Photo-crosslinking is achieved by using one wavelength of light, while a second wavelength of light reversibly cleaves the photo-crosslinked bonds. The effect achieved is that the material may be reversibly switched between an elastomer and a rigid polymer. Examples of photoresponsive switches that can activate the LASMP include cinnamic acid and cinnamylidene acetic acid.

In some embodiments, the SMP may be activated by electrical energy. These SMPs may include carbon nanotubes, short carbon fibers, carbon black, magnetite, metallic Ni powder or SMAs (e.g., TiNi (Nitinol), CuZnAl, FeNiAl alloys), or a combination thereof.

Cannula or Needle

The antifibrotic agent and/or activator can be loaded in a cannula or needle that is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. Some examples of lengths of the cannula or needle may include, but are not limited to, from about 50 to 150 mm in length, for example, about 65 mm for pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula, and/or drug depot can include markings that indicate location at or near the site beneath the skin. Radiographic markers can be included to permit the user to accurately position the needle or cannula, or drug depot into the site of the patient. These radiographic markers will also permit the user to track movement and degradation of the drug depot at the site over time. In this embodiment, the user may accurately position the drug depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In one embodiment, the delivery system for the drug depot can include any syringe based system that would be used to administer a diagnostic imaging agent. These syringe based systems may include inflation syringes with a fine and coarse drive, in conjunction with a pressure gauge. Thus, the drug depot and/or activator can be delivered to the fibrotic tissue in one procedure using the same catheter system.

Administration

In various embodiments, a device (e.g., drug depot) and/or the activator is administered locally to the fibrotic tissue (e.g., hand, knee, bone, muscle, cartilage, etc.). In various embodiments, the drug depot can be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof. Administration may be performed while the patient is at rest or in a distracted position, while standing, laying or sitting.

In various embodiments, because the drug depot is locally administered, therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated. Because the drug depot is administered locally the patient receives treatment at the appropriate site and separate introductions of therapeutic agents are not needed.

The drug depot and/or activator can be delivered to any site beneath the skin, including, but not limited to, at least one muscle, ligament, tendon, cartilage, spinal disc, intrathecal space, thecal sac, blood vessel, spinal foraminal space, near the spinal nerve root, or spinal canal.

Referring to FIG. 1, it illustrates an embodiment of a human radius 8 and ulna 9 in an arm affected by carpal tunnel syndrome. The drug depot 10 containing the antifibrotic agent is implanted near fibrotic tissue by the wrist bone 11. As the drug depot degrades, the antifibrotic agent is released, which degrades or causes the dissolution, shrinkage, relaxation, or stretching of the fibrous or fibrotic tissue or a portion thereof, such as for example, the fibrotic tissue in or surrounding the tendon sheaths that pass through the carpal tunnel, or the fibrous tissue of the flexor retinaculum, which reduces pressure on the median nerve in carpal tunnel syndrome. It will be understood by those of ordinary skill in the art that although the wrist is shown, the antifibrotic agent can be administered to other sites under the skin and to normal or healthy fibrous tissue to relax, degrade, stretch or shrink the tissue which will be beneficial in reducing, preventing or treating pain or inflammation. Therefore, the methods and compositions provided can be used to prevent conditions such as carpal tunnel or tarsal tunnel syndrome, or scoliosis, etc.

Figure 2:
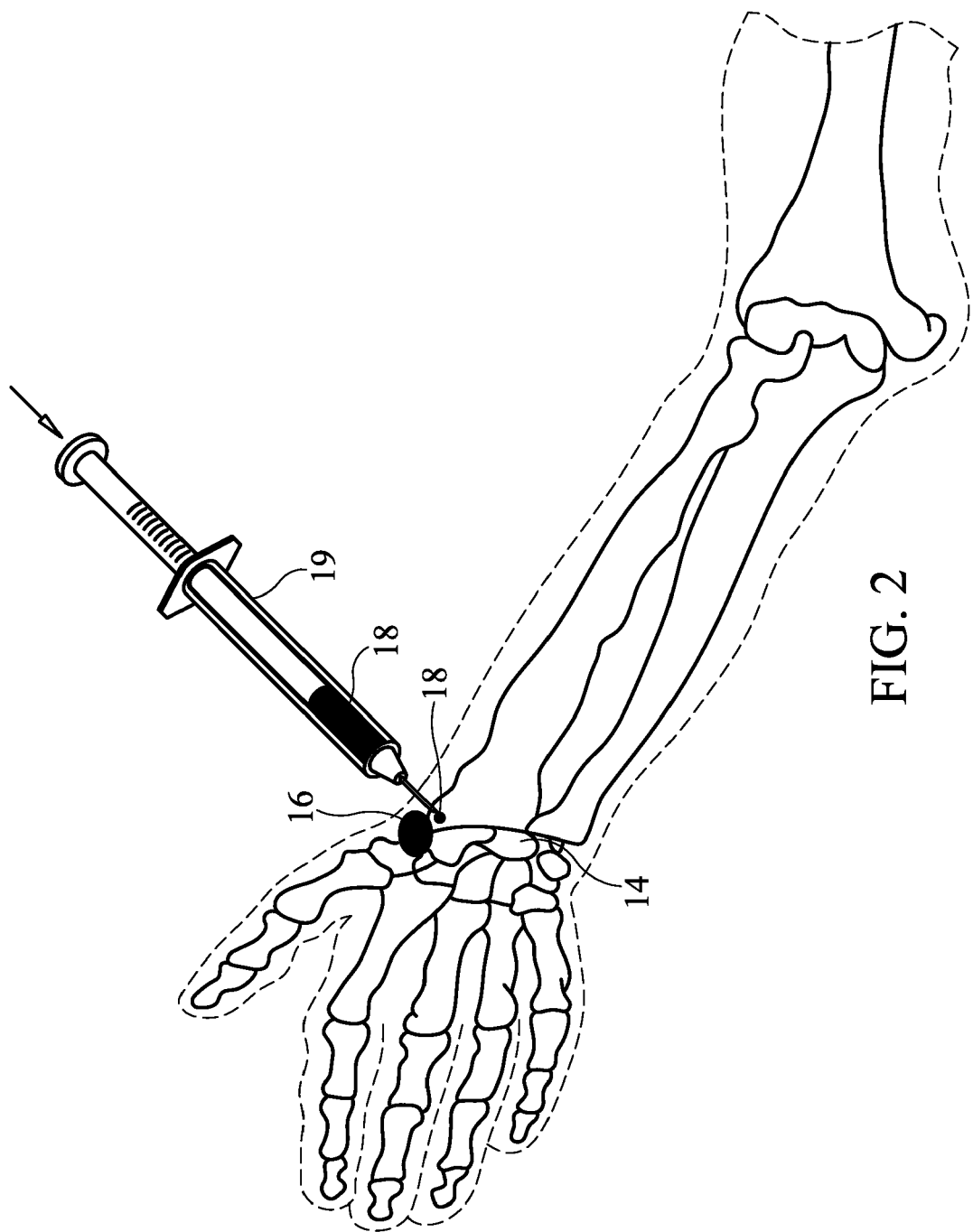
FIG. 2 illustrates an embodiment of a human radius and ulna showing a drug depot containing the antifibrotic agent implanted by the wrist bone near fibrotic tissue and an activator being administered via syringe that causes release of the antifibrotic agent from the drug depot.

FIG. 2 illustrates an embodiment of a human radius and ulna showing a drug depot 16 containing the antifibrotic agent implanted near fibrotic tissue near the wrist bone 14 and an activator 18 being administered locally to the drug depot via syringe 19 having a needle tip at or near the drug depot 16 that causes release of the antifibrotic agent from the drug depot. The antifibrotic agent will be released from the drug depot, which will degrade or cause the dissolution, shrinkage, relaxation, or stretching of a portion of the fibrotic tissue, which reduces pain and/or inflammation associated with carpal tunnel syndrome. The drug depot is configured to immediately release the antifibrotic agent within seconds or minutes to within 24 hours after contact with an activator so that the antifibrotic agent begins to exert its effect and the drug depot is also configured to provide sustained release of the antifibrotic agent as the drug depot degrades. In this way, the antifibrotic agent will stay locally at the target tissue site and will provide treatment for an extended period of time. Thus, one catheter can be used to deliver an "all-in-one composition". The drug depot will also be retrievable in the event it is placed at or near the wrong site because the drug depot will need the activator to release the antifibrotic agent. Therefore, the practitioner can retrieve it because no therapeutic agent has been released or the practitioner has time to move it in the proper location without worry that the therapeutic agent will be prematurely released from the depot.

In some embodiments, the drug depot will polymerize and/or cure in situ, alternatively, they can be administered in solid or semi-solid form. In some embodiments, the drug depot may also contain one or more additional therapeutic agents including a growth factor, an analgesic, an anti-inflammatory agent or a combination thereof.

Figure 3:
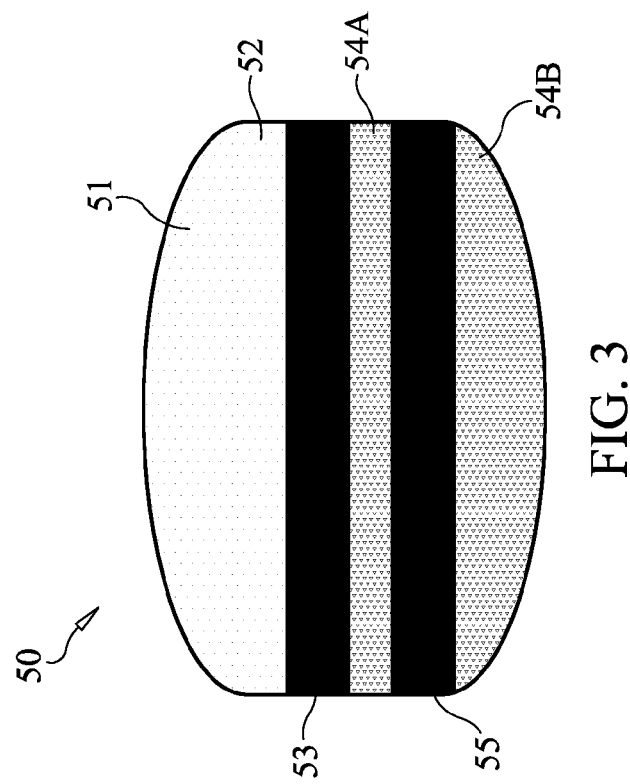
FIG. 3 illustrates an enlarged side sectional view of a drug depot containing an immediate release component that immediately releases an antifibrotic agent and a sustained release component that releases the antifibrotic agent over a prolonged period of time.

FIG. 3 illustrates an enlarged side sectional view of a solid or semi-solid drug depot 50 containing an immediate release layer 51 that is configured on contact with the activator to immediately release a antifibrotic agent 52 as soon as it is implanted within 24 hours and, as the layer degrades, one or more sustained release layers 54A and 54B release the antifibrotic agent over a prolonged period of time (e.g., about 3 days to about 3 months or longer).

Alternatively, the drug depots can be designed with regions that provide immediate release of the same or different therapeutic agent and regions that provide sustain release of the same or different therapeutic agent.

In some embodiments, the drug depot may have one or more additional therapeutic agents disposed in one or more regions that can provide immediate or sustain release of the therapeutic agent. For example, a growth factor, an analgesic, an anti-inflammatory agent or a combination thereof can be disposed in one or more layers 53 and 55 and can be released either in an immediate release or a sustained release fashion after the immediate release layer comprising the antifibrotic agent is released.

In the embodiment shown, the additional therapeutic layer 53 is separate from the immediate release layer 52 and can comprise an anti-inflammatory agent or analgesic that can be in an immediate release formulation to provide immediate relief of pain and/or inflammation locally at the site of implantation. After the additional therapeutic agent is released, a sustained release layer 54A containing the antifibrotic agent can release the antifibrotic agent over an extended period of time. After this layer degrades, an additional therapeutic agent shown as layer 55, such as for example, a growth factor is kept separate from the sustained release layers 54A and 54B containing the antifibrotic agent. This is because, in some embodiments, the antifibrotic agent, which is often an enzyme, can degrade the growth factor. By keeping the growth factor and the antifibrotic agent in a separate layer, premature degradation of the growth factor and/or antifibrotic agent and loss in potency is reduced. After the growth factor 51 is released from the depot and as the layer degrades, the sustained release layer can degrade and continue to release the antifibrotic agent over a prolonged period of time.

Although the drug depot 50 is shown as a five layered depot, it will be understood by one of ordinary skill in the art that the depot can have the antifibrotic agent and additional therapeutic agent disposed in the same or different layers in immediate release or sustained release formulations. In some embodiments, the drug depot can have an immediate release portion and a sustained release portion disposed uniformly distributed through one or more layers of the depot containing the antifibrotic agent alone or in combination with the additional therapeutic agent. In some embodiments, the drug depot can have one, two, three, four, five, six, seven, eight, nine, ten or more layers, where each layer can contain one or more therapeutic agents that can be in an immediate release formulation, sustained release formulation or a combination thereof. A multi-layered or multi-region depot is shown in FIG. 3.

Figure 4:
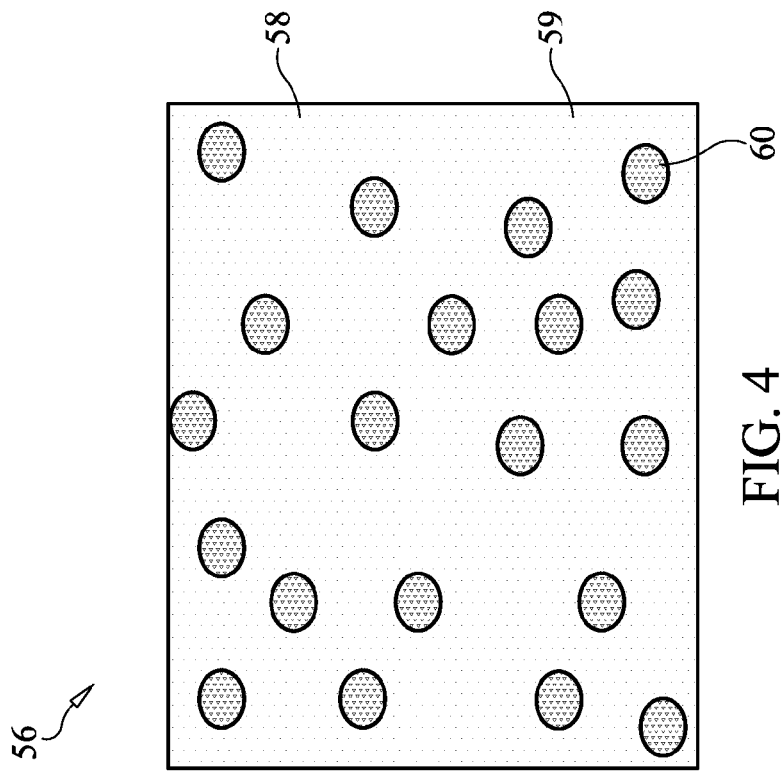
FIG. 4 illustrates an enlarged side sectional view of an embodiment of a drug depot containing an immediate release component that immediately releases an antifibrotic agent on contact with an activator and a sustained release component in microspheres that releases the antifibrotic agent over a prolonged period of time.

FIG. 4 illustrates an enlarged side sectional view of a solid or semi-solid drug depot 56 containing an immediate release layer 58 that is configured to release a antifibrotic agent which is in liquid, semi-solid or solid form when the layer 58 comes in contact with an activator. The activator will cause immediate release of the antifibrotic agent as soon as it contacts immediate release layer 58. After that region degrades, a sustained release microspheres (one shown as 60) releases the antifibrotic agent over a prolonged period of time (e.g., about 3 days to about 3 months or longer).

In some embodiments, the drug depot may have one or more additional therapeutic agents disposed in one or more regions that can provide immediate or sustained release of the therapeutic agent. For example, a growth factor, an analgesic, an anti-inflammatory agent or a combination thereof can be disposed in region 59 or microsphere 60 and be released either in an immediate release or a sustained release fashion as the drug depot 56 degrades.

Although the drug depot 56 is shown as a square shape, it will be understood by one of ordinary skill in the art that the depot can be any shape or it can be amorphous and cure or harden as a depot or it can be a plurality of depots containing the antifibrotic agent in a sustained release formulation. In some embodiments, the drug depots can be uniformly disposed through out the formulation or it can be concentrated in one area of the formulation. In some embodiments, the drug depot will expand and polymerize and/or cure in situ to fill the space at, near, or in the fibrotic tissue.

The techniques and devices described herein provide a safe and effective means for various types of treatment for fibrosis including, but not limited to, degradation, shrinkage, relaxation, or stretching of fibrotic tissue, pain-management, repair, and regeneration. These techniques and devices also allow for the controlled and/or sustained release of desirable active agents within the fibrotic tissue. Further, the techniques and devices described herein can deliver an active agent to a localized area of the fibrotic tissue. The above mentioned techniques and devices can also be used to avoid the potential side effects associated with the direct injection of a solution of an active agent including leakage or overdose. Therefore, the techniques and devices described herein can result in prolonged therapeutic effects while minimizing these and other adverse/side effects.

In some embodiments, the therapeutically effective dosage amount (e.g., antifibrotic agent, analgesic, anti-inflammatory agent, and/or growth factor, etc.) and the release rate profile of the therapeutic agent is sufficient to reduce inflammation and/or pain for a period of at least one day, for example, 1-90 days, 1-10 days, 1-3 days, 3-7 days, 3-12 days; 3-14 days, 3-25 days, 3-45 days, 7-10 days, 7-14 days, 7-21 days, 7-30 days, 7-50 days, 7-90 days, 7-140 days, or 14-140 days, 3 days-3 months, 7 days to 6 months, 10 days to 1 year.

In some embodiments, the therapeutic agent is released from the depot as a bolus dose at the target tissue to provide an immediate release of the therapeutic agent.

In some embodiments, there is a composition useful for the treatment of pain and/or inflammation associated with fibrosis comprising an effective amount of at least one antifibrotic agent alone or in combination with at least one analgesic agent, at least one anti-inflammatory agent, and/or at least one growth factor that is capable of being administered to a target tissue site e.g., a pain or inflammatory site. By way of example, they may be administered locally to one or more fibrotic tissue areas.

In some embodiments, a plurality of depots containing the antifibrotic agent, analgesic, anti-inflammatory agent, and/or growth factor can be placed in and around the fibrotic tissue to provide a strategy to triangulate around the pain generator. A strategy of triangulation may be effective when administering multiple depot pharmaceutical formulations. Thus, a plurality (at least two, at least three, at least four, at least five, at least six, at least seven, etc.) drug depots may be placed around the target tissue site (also known as the pain generator or pain generation site) such that the target tissue site falls within a region that is either between the formulations when there are two, or within an area whose perimeter is defined by a set of plurality of formulations. Alternatively repeat administration to lengthen the delivery timeframe may be required.

In some embodiments, a desired release rate profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days, or at least 1 year.

In some embodiments, the drug depot may release 5%, 10%, 15%, 20%, 25%, 30%, 40%, 50%, 60%, 70%, 80%, 90%, 95%, or 99% of the therapeutic agent (e.g., antifibrotic agent) or pharmaceutically acceptable salt thereof relative to a total amount of the therapeutic agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days, or at least 1 year.

In various embodiments, the antifibrotic agent, analgesic, anti-inflammatory agent, and/or growth factor will be released in an initial burst dose when it contacts an activator, then one or more of these therapeutic agents will be released daily for 3 days and then stop (e.g., this will be suitable to reduce, prevent or treat, acute pain), while the antifibrotic agent, analgesic, anti-inflammatory agent, and/or growth factor will be released daily without a burst dose for 3 to 12 days, 5 to 10 days or 7 to 10 days or longer after the drug depot is administered to the target tissue site.

In various embodiments, a kit is provided comprising one or more drug depots containing one or more antifibrotic agents, analgesics, anti-inflammatory agents, and/or growth factors. The kit may also include additional parts along with the drug depots combined together to be used to administer it. The kit may include the drug depot and delivery device in a first compartment along with an activator. The second compartment may include a canister holding the drug depots and any other instruments needed for the localized drug delivery.

A third compartment may include gloves, drapes, needles, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Method of Making Drug Depots

In various embodiments, the drug depot comprising the active ingredients (e.g., the antifibrotic agent, analgesic, anti-inflammatory agent, growth factor, and/or activator) can be made by combining a biocompatible polymer and a therapeutically effective amount of the active ingredients or pharmaceutically acceptable salts thereof and forming the drug depot from the combination.

Where solution processing techniques are used to make the drug depot, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent (e.g., the antifibrotic agent, analgesic, anti-inflammatory agent, and/or growth factor), and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with the therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., hyaluronidase), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., room temperature), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures may result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where water-soluble therapeutic agents are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this release profile is not desired. Thus, a sustained release region of the drug depot may, in various embodiments, be made by immediate removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least antifibrotic agent, analgesic, anti-inflammatory agent, and/or growth factor or pharmaceutically acceptable salt thereof and forming the implantable drug depot from the combination.

In some embodiments, the therapeutic agent can be incorporated into a depot in the form of microspheres, nanospheres, etc. Examples of apparatus and aseptic procedures useful for the formation of sterile microspheres are described, e.g., in U.S. Pat. Nos. 5,945,126; 6,270,802; and 6,361,798, the disclosures of which are hereby incorporated by reference. These microspheres can then be dispersed or mixed and formed into the drug depot.

Microspheres can be made by a number of techniques, such as single and double emulsion, suspension polymerization, solvent evaporation, spray drying, and solvent extraction. Methods for making microspheres are described in the literature, for example, in Mathiowitz and Langer, J. Controlled Release 5:13-22 (1987); Mathiowitz et al., Reactive Polymers 6:275-283 (1987); Mathiowitz et al., J. Appl. Polymer Sci. 35:755-774 (1988); Mathiowitz et al., Scanning Microscopy 4:329-340 (1990); Mathiowitz et al., J. Appl. Polymer Sci., 45:125-134 (1992); and Benita et al., J. Pharm. Sci. 73:1721-1724 (1984).

In solvent evaporation, described for example in Mathiowitz et al., (1990), Benita et al. (1984), and U.S. Pat. No. 4,272,398, the macromers are dissolved in a solvent. If desired, an agent to be incorporated, either in soluble form or dispersed as fine particles, is added to the macromer solution, and the mixture is suspended in an aqueous phase that contains a surface active agent. The resulting emulsion is stirred until most of the solvent evaporates, leaving solid microspheres, which may be washed with water and dried overnight in a lyophilizer. The microspheres are polymerized, for example, by exposure to light.

In solvent removal, the macromers are dissolved in a solvent. The mixture can then be suspended in oil, such as silicon oil, by stirring, to form an emulsion. As the solvent diffuses into the oil phase, the emulsion droplets harden into solid polymer microspheres. The microspheres can be polymerized by exposure to light, for example.

Spray drying is implemented by passing the polymerizable macromers through a nozzle, spinning disk or equivalent device to atomize the mixture to form fine droplets. The polymerizable macromers may be provided in a solution or suspension, such as an aqueous solution. The fine droplets are exposed to light, for example, to cause polymerization of the macromer and formation of the microspheres.

In another embodiment, microspheres are prepared by a water-in-oil emulsion or suspension process, wherein the polymerizable macromers and the substance to be incorporated, if desired, are suspended in a water-in-oil suspension and exposed to light to polymerize the macromers to form particles incorporating the substance, such as the therapeutic agent.

In another embodiment, microspheres can be formed by atomizing macromer solution into oil, followed by polymerization.

In some embodiments, the drug depots are loaded into the formulation and are disposed uniformly throughout it or in a particular region (e.g., center or borders) and delivered in, at, or near the fibrotic tissue. The drug depot will degrade and release the therapeutic agent at, near or in the fibrotic tissue. For example, the drug depot will begin releasing the antifibrotic agent immediately or in a sustained release fashion to degrade the fibrotic tissue of the kidney, lung, liver, skin, central nervous system, bone, bone marrow, cartilage, muscle, cardiovascular, endocrine, and/or gastrointestinal system.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for treating fibrous tissue in a patient in need of such treatment, the device being biodegradable and implantable at, near, or in a fibrous tissue, the device comprising an antifibrotic agent to degrade, shrink, relax or stretch at least a portion of the fibrous tissue and being configured to immediately release an effective amount of the antifibrotic agent within 24 hours and configured to provide sustained release of the antifibrotic agent over a period of up to one year to treat the fibrous tissue, the antifibrotic agent comprising hyaluronidase or relaxin and the effective amount is 0.05 mg/kg to 0.8 mg/kg.

2. A device according to claim 1, wherein the device comprises a drug depot that releases the antifibrotic agent over a period of at least 3 days to 3 months to treat normal fibrous tissue or abnormal fibrous tissue.

3. A device according to claim 2, wherein the drug depot comprises an immediate release component that releases the antifibrotic agent within 24 hours and a sustained release component that releases the antifibrotic agent over a period of at least 3 days to 3months after implantation.

4. A device according to claim 2, wherein the drug depot comprises a polymer and the polymer comprises about 60% to 99% of the total weight % of the drug depot and the antifibrotic agent reduces fibrosis and relaxes the flexor retinaculum in carpal tunnel syndrome or degrades. relaxes or stretches fibrous tissue in scoliosis.

5. A device according to claim 1, wherein the device is a drug depot that releases (i) a bolus dose of the antifibrotic agent within the fibrous tissue over a period of up to 3 days and (ii) a sustained release dose of the antifibrotic agent within the fibrous tissue over a period of up to 3months.

6. A device according to claim 1, wherein the device releases about 20% to about 99% of the antifibrotic agent relative to a total amount of the antifibrotic agent loaded in the device over a period of 3 days to 12 months after the device is administered within the within the fibrous tissue.

7. A device according to claim 2, wherein the drug depot further comprises a growth factor, an analgesic, an anti-inflammatory agent or a combination thereof.

8. A device according to claim 7, wherein the growth factor is disposed in one or more components that are separate from the immediate release component and the sustained release component of the drug depot.

9. A device according to claim 2, wherein the drug depot comprises at least one biodegradable polymer comprising one or more of poly(lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone or a combination thereof.

10. A device according to claim 2, wherein the drug depot is polymerizable in-situ or curable in-situ within the fibrous tissue.

11. A device according to claim 1, wherein the patient suffers from a localized fibrosis associated with stenosing tenosynovitis, Dupuytren's disease, Ledderhose's disease, Peyronie's disease, fibromatosis colli, keloids, or mediastinal fibrosis.

12. A device for treating fibrous tissue in a patient in need of such treatment, the device being biodegradable and implantable at, near, or in a fibrous tissue, the device comprising an antifibrotic agent to degrade, shrink, relax or stretch at least a portion of the fibrous tissue and being configured to immediately release an effective amount of the antifibrotic agent within 24 hours; and an activator configured to contact the device and cause immediate release of the antifibrotic agent, the antifibrotic agent comprising hyaluronidase or relaxin and the effective amount is 0.05 mg/kg to 0.8 mg/kg.

13. A device according to claim 12, wherein the device comprises a drug depot and the activator comprises (i) a liquid that degrades at least a portion of the drug depot and causes immediate release of the antifibrotic agent; or (ii) an electrical signal, electromagnetic radiation, magnetic field, acoustic energy, or ultrasonic energy applied at, near or to the drug depot and causes immediate release of the antifibrotic agent, wherein the drug depot comprises a shape memory polymer.

14. A device according to claim 13, wherein at least one of: (i) the liquid is at a temperature of 30 to 45° C. to cause immediate release of the antifibrotic agent; (ii) the liquid comprises a buffer that causes a pH change to cause immediate release of the antifibrotic agent; (iii) the liquid comprises a salt that causes immediate release of the antifibrotic agent; or (iv) the liquid comprises a sufficient concentration of metal ions that causes immediate release of the antifibrotic agent.

15. A device according to claim 13, wherein the drug depot comprises an immediate release component that releases the antifibrotic agent within 24 hours after contact with the activator and a sustained release component that releases the antifibrotic agent over a period of at least 3 days to 3 months after implantation.

16. A device according to claim 12, wherein the device is configured to provide sustained release of the antifibrotic agent over a period of up to one year to treat the fibrous tissue and the drug depot releases (i) a bolus dose of the antifibrotic agent within the fibrous tissue over a period of up to 3 days after contact with the activator; and (ii) a sustained release dose of the antifibrotic agent within the fibrous tissue over a period of up to 3 months.

17. A device according to claim 12, wherein the device is configured to provide sustained release of the antifibrotic agent over a period of up to one year to treat the fibrous tissue and the device releases about 20% to about 99% of the antifibrotic agent relative to a total amount of the antifibrotic agent loaded in the device over a period of 3 days to 12months after the device is administered within the fibrous tissue.

* * * * *